(12) United States Patent
Mei et al.

(10) Patent No.: US 11,150,251 B2
(45) Date of Patent: Oct. 19, 2021

(54) BI-FUNCTIONAL ARGININE-GLYCINE-ASPARTIC ACID (RGD) PEPTIDES AND METHODS TO PROMOTE ANGIOGENESIS

(71) Applicants: Clemson University Research Foundation, Clemson, SC (US); MUSC Foundation for Research Development, Charleston, SC (US)

(72) Inventors: Ying Mei, Mount Pleasant, SC (US); Jia Jia, Charleston, SC (US); Chung-Jen James Chou, Mount Pleasant, SC (US)

(73) Assignees: Clemson University Research Foundation, Clemson, SC (US); MUSC Foundation for Research Development, Charleston, SC (US)

( * ) Notice: Subject to any disclaimer, the term of this patent is extended or adjusted under 35 U.S.C. 154(b) by 167 days.

(21) Appl. No.: 15/726,766

(22) Filed: Oct. 6, 2017

(65) Prior Publication Data
US 2018/0120332 A1 May 3, 2018

Related U.S. Application Data

(60) Provisional application No. 62/405,523, filed on Oct. 7, 2016.

(51) Int. Cl.
| | | |
|---|---|---|
| *G01N 33/68* | (2006.01) | |
| *C07K 7/06* | (2006.01) | |
| *C07K 7/08* | (2006.01) | |
| *A61P 9/10* | (2006.01) | |
| *G01N 33/74* | (2006.01) | |
| *C07K 14/78* | (2006.01) | |
| *C07K 17/02* | (2006.01) | |
| *C07K 14/71* | (2006.01) | |
| *C07K 14/755* | (2006.01) | |
| *C07K 14/52* | (2006.01) | |
| *C07K 14/75* | (2006.01) | |
| *C07K 14/705* | (2006.01) | |
| *A61K 38/00* | (2006.01) | |

(52) U.S. Cl.
CPC ............ *G01N 33/6893* (2013.01); *A61P 9/10* (2018.01); *C07K 7/06* (2013.01); *C07K 7/08* (2013.01); *C07K 14/52* (2013.01); *C07K 14/70546* (2013.01); *C07K 14/71* (2013.01); *C07K 14/75* (2013.01); *C07K 14/755* (2013.01); *C07K 14/78* (2013.01); *C07K 17/02* (2013.01); *G01N 33/74* (2013.01); *A61K 38/00* (2013.01); *G01N 2333/70557* (2013.01); *G01N 2333/70596* (2013.01); *G01N 2500/04* (2013.01); *G01N 2500/20* (2013.01); *G01N 2800/7014* (2013.01)

(58) Field of Classification Search
None
See application file for complete search history.

(56) References Cited

U.S. PATENT DOCUMENTS

| | | | |
|---|---|---|---|
| 5,147,797 A | 9/1992 | McCarthy et al. | |
| 5,294,551 A | 3/1994 | Furcht et al. | |
| 5,330,911 A | 7/1994 | Hubbell et al. | |
| 5,834,029 A | 11/1998 | Bellamkonda et al. | |
| 6,156,572 A | 12/2000 | Bellamkonda et al. | |
| 7,041,506 B2 | 5/2006 | Campbell et al. | |
| 2008/0044900 A1 | 2/2008 | Mooney et al. | |

FOREIGN PATENT DOCUMENTS

JP     2015528493     *  9/2015

OTHER PUBLICATIONS

Salimath et al. ("Dual Delivery of Hepatocyte and Vascular Endothelial Growth Factors via a Protease-Degradable Hydrogel Improves Cardiac Function in Rats" PLOS ONE Nov. 2012; vol. 7, Issue 11).*
Ahmad et al. (Peptide Cross-linked Poly (Ethylene Glycol) Hydrogel Films as Biosensor Coating for the Detection of Collagenase Sensors 2019, 19 1677).*
Liu et al. (Synthesis of an RGD-grafter oxidized sodium alginate-N-succinyl chitosan hydrogel and an in vitro study of endothelial and osteogenic differentiation Journal of Materials Chemistry B 2013, 1, 4484-4492).*
Yamada et al. ("Laminin-11-derived peptide-hyaluronate hydrogels as a synthetic basement membrane" Biomaterials 34 (2013) 6539-6547).*
By Barbick et al. ("The promotion of microvasculature formation in poly(ethylene glycol) diacrylate hydrogels by an immobilized VEGF-mimetic peptide" Biomaterials 32 (2011) 5782-5789).*
Lee et al. ("Alginate: properties and biomedical applications"; Prog Polym Sci 2012; 37(1): 106-126).*
Over Zisch et al. ("Cell-demanded release of VEGF from synthetic, biointeractive cell-ingrowth matrices for vascularized tissue growth" The FASEB Journal express article. Published online Oct. 16, 2003).*
Chen et al. ("A laminin mimetic peptide SIKVAV-conjugated chitosan hydrogel promoting wound healing by enhancing angiogenesis, re-epithelialization and collagen deposition" J. Mater.Chem.2015, 3, 6798, published Jul. 8, 2015).*

(Continued)

*Primary Examiner* — James H Alstrum-Acevedo
*Assistant Examiner* — Tara L Martinez
(74) *Attorney, Agent, or Firm* — Myers Bigel, P.A.

(57) ABSTRACT

The present invention provides an in vitro method for identifying a compound that promotes endothelial cell adhesion, endothelial cell spreading, endothelial cell migration and/or endothelial cell proliferation for the manufacture of a diagnostic or therapeutic agent. The present invention further provides the identified compounds and pharmaceutical compositions, and assays and kits for identifying a compound or using a compound that promotes endothelial cell adhesion, endothelial cell spreading, endothelial cell migration and/or endothelial cell proliferation and is useful for bioprinting.

14 Claims, 15 Drawing Sheets

Specification includes a Sequence Listing.

(56) References Cited

OTHER PUBLICATIONS

Akiyama et al. "Analysis of Fibronectin Receptor Function with Monoclonal Antibodies: Roles in Cell Adhesion, Migration, Matrix Assembly, and Cytoskeletal Organization" *The Journal of Cell Biology* 109:863-875 (1989).
Anderson et al. "Nanoliter-scale synthesis of arrayed biomaterials and application to human embryonic stem cells" *Nature Biotechnology* 22(7):863-866 (2004) (Abstract only).
Anderson et al. "Biomaterial microarrays: rapid, microscale screening of polymer-cell interaction" *Biomaterials* 26:4892-4897 (2005).
Ayres et al. "Elastin-Based Side-Chain Polymers Synthesized by ATRP" *Macromolecules* 36(16):5967-5973 (2003) (Abstract only).
Bidarra et al. "Injectable in situ crosslinkable RGD-modified alginate matrix for endothelial cells delivery" *Biomaterials* 32(31):7897-7904 (2011) (Abstract only).
Blatchley et al. "Acellular implantable and injectable hydrogels for vascular regeneration" *Biomedical Materials* 10:034001 (2015).
Bouhadir et al. "Degradation of Partially Oxidized Alginate and Its Potential Application for Tissue Engineering" *Biotechnology Progress* 17:945-950 (2001).
Briquez et al. "Design principles for therapeutic angiogenic materials" *Nature Reviews Materials* 1:15006 (2016) (Abstract only).
Burdick et al. "Photoencapsulation of osteoblasts in injectable RGD-modified PEG hydrogels for bone tissue engineering" *Biomaterials* 23(22):4315-4323 (2002) (Abstract only).
Burridge et al. "Chemically Defined Generation of Human Cardiomyocytes" *Nature Methods* 11(8):855-860 (2014).
Celiz et al. "Materials for stem cell factories of the future" *Nature Materials* 13(6):570-579 (2014) (Abstract only).
Chong et al. "Human Embryonic Stem Cell-Derived Cardiomyocytes Regenerate Non-Human Primate Hearts" *Nature* 510(7504):273-277 (2014).
Cook, Wayne D. "Photopolymerization kinetics of dimethacrylates using the camphorquinone/amine initiator system" *Polymer* 33(3):600-609 (1992) (Abstract only).
Davis et al. "Endothelial Extracellular Matrix: Biosynthesis, Remodeling, and Functions During Vascular Morphogenesis and Neovessel Stabilization" *Circulation Research* 97:1093-1107 (2005).
Deforest et al. "Cytocompatible Click-based Hydrogels with Dynamically-Tunable Properties Through Orthogonal Photoconjugation and Photocleavage Reactions" *Nature Chemistry* 3(12):925-931 (2011).
Dequach et al. "Injectable skeletal muscle matrix hydrogel promotes neovascularization and muscle cell infiltration in a hindlimb ischemia model" *European Cells & Materials* 23:400-412 (2012).
D'Souza et al. "Arginyl-glycyl-aspartic acid (RGD): a cell adhesion motif" *Trends in Biochemical Sciences* 16(7):246-250 (1991) (Abstract only).
Fondevila et al. "Cyclic RGD peptides with high affinity for alpha5beta1 integrin protect genetically fat Zucker rat livers from cold ischemia/reperfusion injury" *Transplantation Proceedings* 37(4):1679-1681 (2005) (Abstract only).
Goujon et al. "A new bioinformatics analysis tools framework at EMBL—EBI" *Nucleic Acids Research* 38:W695-W699 (2010).
Hern et al. "Incorporation of adhesion peptides into nonadhesive hydrogels useful for tissue resurfacing" *Journal of Biomedical Materials Research* 39(2):266-276 (1998) (Abstract only).
Herron et al. "Extracellular Matrix Mediated Maturation of Human Pluripotent Stem Cell Derived Cardiac Monolayer Structure and Electrophysiological Function" *Circulation Arrhythmia and Electrophysiology* 9(4):1-23 (2016).
Humphries et al. "Integrin Ligands" *Journal of Cell Science* 119(Pt 19):3901-3903 (2006).
Jeon et al. "Protein-surface interactions in the presence of polyethylene oxide—I. Simplified theory" *Journal of Colloid and Interface Science* 142(1):149-158 (1991) (Abstract only).
Jia et al. "Engineering alginate as bioink for bioprinting" *Acta Biomaterialia* 10(10):4323-4331 (2014).

Jia et al. "Development of peptide-functionalized synthetic hydrogel microarrays for stem cell and tissue engineering applications" *Acta Biomaterialia* 45:110-120 (2016).
Kireeva et al. "Adhesion of Human Umbilical Vein Endothelial Cells to the Immediate-Early Gene Product Cyr61 Is Mediated Through Integrin $\alpha v \beta_3$" *The Journal of Biological Chemistry* 273(5):3090-3096 (1998).
Kouvroukoglou et al. "Endothelial cell migration on surfaces modified with immobilized adhesive peptides" *Biomaterials* 21(17):1725-1733 (2000) (Abstract only).
Kumagai et al. "Effect of cyclic RGD peptide on cell adhesion and tumor metastasis" *Biochemical and Biophysical Research Communications* 177(1):74-82 (1991) (Abstract only).
Kumar et al. "Treatment of hind limb ischemia using angiogenic peptide nanofibers" *Biomaterials* 98:113-119 (2016).
Laflamme et al. "Cardiomyocytes derived from human embryonic stem cells in pro-survival factors enhance function of infarcted rat hearts" *Nature Biotechnology* 25:1015-1024 (2007) (Abstract only).
Lamalice et al. "Endothelial Cell Migration During Angiogenesis" *Circulation Research* 100:782-794 (2007).
Landa et al. "Effect of Injectable Alginate Implant on Cardiac Remodeling and Function After Recent and Old Infarcts in Rat" *Circulation* 117:1388-1396 (2008).
Lee et al. "The effect of spacer arm length of an adhesion ligand coupled to an alginate gel on the control of fibroblast phenotype" *Biomaterials* 31(21):5545-5551 (2010) (Abstract only).
Leslie-Barbick et al. "The promotion of microvasculature formation in poly(ethylene glycol) diacrylate hydrogels by an immobilized VEGF-mimetic peptide" *Biomaterials* 32(35):5782-5789 (2011) (Abstract only).
Loose et al. "A linguistic model for the rational design of antimicrobial peptides" *Nature* 443(7113):867-869 (2006) (Abstract only).
Lum et al. "Regulation of vascular endothelial barrier function" *American Journal of Physiology-Lung Cellular and Molecular Physiology* 267:L223-L241 (1994).
Martino et al. "Engineering the Growth Factor Microenvironment with Fibronectin Domains to Promote Wound and Bone Tissue Healing" *Science Translational Medicine* 3(100):100ra89 (2011).
McWilliam et al. "Analysis Tool Web Services from the EMBL-EBI" *Nucleic Acids Research* 41:W597-W600 (2013).
Mei et al. "Mapping the Interactions among Biomaterials, Adsorbed Proteins, and Human Embryonic Stem Cells" *Advanced Materials* 21:2781-2786 (2009).
Mei et al. "Combinatorial Development of Biomaterials for Clonal Growth of Human Pluripotent Stem Cells" *Nature Materials* 9(9):768-778 (2010).
Melkoumian et al. "Synthetic peptide-acrylate surfaces for long-term self-renewal and cardiomyocyte differentiation of human embryonic stem cells" *Nature Biotechnology* 28(6):606-610 (2010) (Abstract only).
Meredith et al. "Integrins, adhesion and apoptosis" *Trends in Cell Biology* 7(4):146-150 (1997) (Abstract only).
Moon et al. "Biomimetic hydrogels with pro-angiogenic properties" *Biomaterials* 31(14):3840-3847 (2010).
Mordwinkin et al. "A Review of Human Pluripotent Stem Cell-Derived Cardiomyocytes for High-Throughput Drug Discovery, Cardiotoxicity Screening, and Publication Standards" *Journal of Cardiovascular Translational Research* 6(1):22-30 (2013).
Netzel-Arnett et al. "Sequence Specificities of Human Fibroblast and Neutrophil Collagenases" *The Journal of Biological Chemistry* 266(11):6747-6755 (1991).
Park et al. "Photopolymerized hyaluronic acid-based hydrogels and interpenetrating networks" *Biomaterials* 24(6):893-900 (2003) (Abstract only).
Park et al. "Harnessing developmental processes for vascular engineering and regeneration" *Development* 141:2760-2769 (2014).
Pataky et al. "Microdrop printing of hydrogel bioinks into 3D tissue-like geometries" *Advanced Materials* 24(3):391-396 (2012) (Abstract only).
Pechar et al. "The coiled coil motif in polymer drug delivery systems" *Biotechnology Advances* 31(1):90-96 (2013) (Abstract only).

(56) References Cited

OTHER PUBLICATIONS

Pierschbacher et al. "Cell attachment activity of fibronectin can be duplicated by small synthetic fragments of the molecule" *Nature* 309(5963):30-33 (1984) (Abstract only).
Roche et al. "Comparison of biomaterial delivery vehicles for improving acute retention of stem cells in the infarcted heart" *Biomaterials* 35(25):6850-6858 (2014).
Roger et al. "Heart Disease and Stroke Statistics—2011 Update: A Report From the American Heart Association" *Circulation* 123(4):e18-e209 (2011).
Rowley et al. "Alginate hydrogels as synthetic extracellular matrix materials" *Biomaterials* 20:45-53 (1999) (Abstract only).
Sallam et al. "Modeling Inherited Cardiac Disorders—A Cell Is Worth a Thousand Genes" *Circulation Journal* 78:784-794 (2014).
Sasaki et al. "Domain IVa of laminin α5 chain is cell-adhesive and binds β1 and αVβ3 integrins through Arg-Gly-Asp" *FEBS Letters* 509:181-185 (2001).
Satake et al. "Angiogenic stimuli are essential for survival of vascular endothelial cells in three-dimensional collagen lattice" *Biochemical and Biophysical Research-Communications* 244(3):642-646 (1998) (Abstract only).
Serbo et al. "Vascular tissue engineering: biodegradable scaffold platforms to promote angiogenesis" *Stem Cell Research & Therapy* 4:1-8 (2013).
Sievers et al. "Fast, scalable generation of high-quality protein multiple sequence alignments using Clustal Omega" *Molecular Systems Biology* 7(539):1-6 (2011).
Silva et al. "Effects of VEGF Temporal and Spatial Presentation on Angiogenesis" *Biomaterials* 31 (6):1235 (2010).
Simmons et al. "Dual growth factor delivery and controlled scaffold degradation enhance in vivo bone formation by transplanted bone marrow stromal cells" *Bone* 35(2):562-569 (2004) (Abstract only).
Singh et al. "Capillary Morphogenesis in PEG-Collagen Hydrogels" *Biomaterials* 34(37):9331-9340 (2013).
Söding, Johannes "Protein homology detection by HMM-HMM comparison" *Bioinformatics* 21(7):951-960 (2005).
Tashiro et al. "The RGD containing site of the mouse laminin A chain is active for cell attachment, spreading, migration and neurite outgrowth" *Journal of Cellular Physiology* 146(3):451-459 (1991) (Abstract only).
Thomson et al. "Embryonic Stem Cell Lines Derived from Human Blastocysts" *Science* 282(5391):1145-1147 (1998).
Tong et al. "Controlling the Fibroblastic Differentiation of Mesenchymal Stem Cells via the Combination of Fibrous Scaffolds and Connective Tissue Growth Factor" *Tissue Engineering Part A* 17(21 & 22):2773-2785 (2011).
Tziampazis et al. "PEG-variant biomaterials as selectively adhesive protein templates: model surfaces for controlled cell adhesion and migration" *Biomaterials* 21:511-520 (2000).
Ungerleider et al. "Extracellular Matrix Hydrogel Promotes Tissue Remodeling, Arteriogenesis, and Perfusion in a Rat Hindlimb Ischemia Model" *JACC Basic to Translational Science* 1(1-2):32-44 (2016).
Van Hove et al. "Temporally Tunable, Enzymatically-responsive Delivery of Pro-angiogenic Peptides from Poly(ethylene glycol) Hydrogels" *Advanced Healthcare Materials* 4(13):2002-2011 (2015).
Weeks et al. "Adult and fetal human mesangial cells interact with specific laminin domains" *American Journal of Physiology* 261:F688-F695 (1991).
Yamada et al. "Structural and Functional Analyses of the Arg-Gly-Asp Sequence Introduced into Human Lysozyme" *The Journal of Biological Chemistry* 268(14):10588-10592 (1993).
Zanotelli et al. "Stable engineered vascular networks from human induced pluripotent stem cell-derived endothelial cells cultured in synthetic hydrogels" *Acta Biomaterialia* 35:32-41 (2016).
Zhu, Junmin "Bioactive Modification of Poly(ethylene glycol) Hydrogels for Tissue Engineering" *Biomaterials* 31(17):4639-4656 (2010).
Zumbuehl et al. "Antifungal hydrogels" *Proceedings of the National Academy of Sciences USA* 104(32):12994-12998 (2007).

\* cited by examiner

| Molecular Origin | Peptides |
|---|---|
| Laminin-α1 | DVEK*RGD*REEAHVP(α1) |
| Laminin-α3 | IQ*RGD*IDAMIS(α3) |
| Laminin-α4 | DAVKQLQAAE*RGD*A(α4) |
| Laminin-α5 | SETQ*RGD*VFVP(α5-1), PASY*RGD*SC(α5-2) |
| Laminin-β4 | PMQKM*RGD*VFSP(β4) |
| Laminin-γ2 | *R*SDGTG(γ2) |
| Laminin-γ3 | EAP*RGD*VYQG(γ3) |
| Fibronectin | VTG*RGD*SPAS(Fn), *RGD*SP |
| Vitronectin | PQVT*RGD*VFTMP(Vn), T*RGD*VFT |

| Molecular Origin | Peptides |
|---|---|
| Laminin-α1 | TFALRGDNP(α1)<br>DVEKRGDREEAHVP(α1-2) |
| Laminin-α3 | IQRGDIDAMIS(α3) |
| Laminin-α4 | DAVKQLQAAERGDA(α4) |
| Laminin-α5 | SETQRGDVFVP(α5-1), PASYRGDSC(α5-2) |
| Laminin-β4 | PMQKMRGDVFSP(β4) |
| Laminin-γ2 | RSDGTG(γ2) |
| Laminin-γ3 | EAPRGDVYQG(γ3) |
| Fibronectin | VTGRGDSPAS(Fn), RGDSP, RGDS |
| Vitronectin | PQVTRGDVFTMP(Vn), TRGDVFT |

FIG. 7

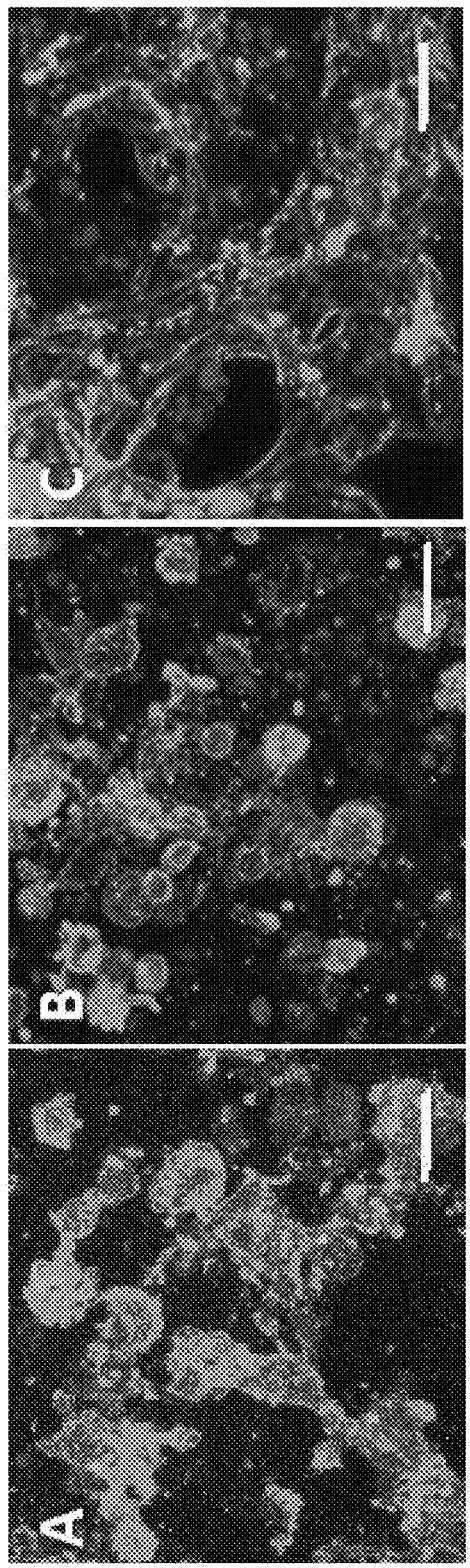
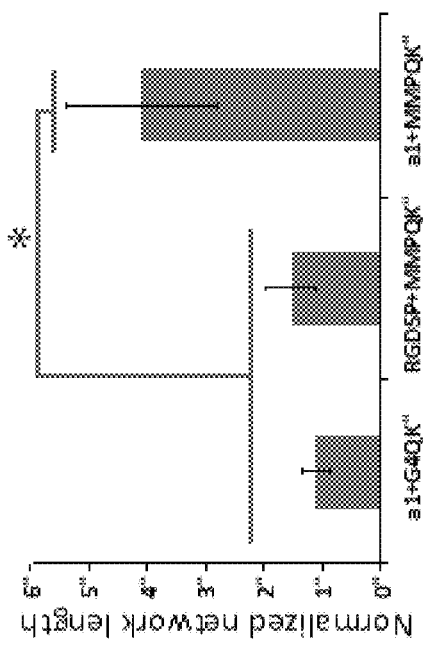
FIG. 11A  FIG. 11B  FIG. 11C  FIG. 11D

US 11,150,251 B2

BI-FUNCTIONAL ARGININE-GLYCINE-ASPARTIC ACID (RGD) PEPTIDES AND METHODS TO PROMOTE ANGIOGENESIS

STATEMENT OF PRIORITY

This application claims the benefit, under 35 U.S.C. § 119(e), of U.S. Provisional Application Ser. No. 62/405,523, filed Oct. 7, 2016, the entire contents of which are incorporated by reference herein.

STATEMENT OF GOVERNMENT SUPPORT

This invention was made with government support under grant numbers GM103444 and GM104941 awarded by The National Institutes of Health and grant number EPS-0903795 awarded by the National Science Foundation. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 9662-68_ST25.txt, 10,245 bytes in size, generated on Jan. 16, 2018 and filed via EFS-Web, is provided in lieu of a paper copy. This Sequence Listing is hereby incorporated by reference herein into the specification for its disclosures.

RESERVATION OF COPYRIGHT

A portion of the disclosure of this patent document contains material which is subject to copyright protection. The copyright owner, Clemson University or MUSC Foundation for Research Development, has no objection to the reproduction by anyone of the patent document or the patent disclosure, as it appears in the U.S. Patent and Trademark Office patent file or records, but otherwise reserves all copyright rights whatsoever.

FIELD OF THE INVENTION

The present invention relates to arginine-glycine-aspartic acid (RGD) peptide compounds and methods and assays for identifying compounds, in particular, RGD peptides, that bind to and/or modulate a cell surface integrin and compounds and methods to promote angiogenesis.

BACKGROUND OF THE INVENTION

Vasculature plays an essential role in maintaining normal tissue functions through the delivery of oxygen and nutrients and removal of the waste generated by the tissues. Ischemic diseases that affect normal blood supply pose an enormous threat to public health. In the heart, lack of sufficient blood supply leads to cell death and permanent loss of heart functions. Each year, 7.2 million people die from ischemic heart disease (IHD), which accounts for 12% of all reported deaths worldwide. In addition to cardiovascular disease, periphery artery, carotid artery, renal artery and venous diseases can all lead to serious illness, even death. It was estimated that over 300 million patients would benefit from pro-angiogenic therapies in western nations. To address this concern, significant efforts have been devoted to developing functional biomaterials to recreate natural vasculogenic (i.e., de novo vessel formation) and angiogenic (i.e., new vessel formed from pre-existing vessels) environments to promote neovascularization. To this end, numerous pro-vascularization growth factors (e.g., VEGF and bFGF) have been incorporated into hydrogels to achieve controlled, local delivery. In parallel, cell adhesive peptides (e.g., RGDS (SEQ ID NO:35)/RGDSP (SEQ ID NO:34)) have been conjugated onto hydrogels to improve their affinity to endothelial cells. The RGDS (SEQ ID NO:35)/RGDSP (SEQ ID NO:34) peptides enhance the binding affinity of the constructs to $\alpha_v\beta_3$ integrin expressed on endothelial cells (EC) and improve EC adhesion, spreading and proliferation. Further, recent studies showed the hydrogels functionalized with RGDS (SEQ ID NO:35)/RGDSP (SEQ ID NO:34) peptides initiate integrin-mediated signaling pathway, induce up-regulation of VEGF receptor 2 (VEGFR2) and result in improved EC proliferation and migration in vitro and improved angiogenesis in vivo.

While RGDS (SEQ ID NO:35)/RGDSP (SEQ ID NO:34) peptides derived from the cell adhesive domain of Fibronectin (Fn) have been extensively used to promote EC functions (e.g., adhesion, spreading, proliferation, migration), their affinity to EC integrin is rather moderate, which leads to suboptimal EC functions. For example, RGDS (SEQ ID NO:35) peptide functionalization has been repeatedly used to promote EC attachment and spreading in both 2D and 3D environments. However, ECs undergo apoptosis by 28-72 hrs after seeding without high concentrations of angiogenic factors. This highlights an urgent need to identify novel RGD (SEQ ID NO:36) peptides with high affinity to EC integrin to improve their functions.

In nature, vascular endothelium supports the dynamic functionality of ECs. The extracellular matrix (ECM) proteins in the vascular endothelium, including laminin (Ln), fibronectin (Fn), vitronectin (Vn) and collagen, have been shown to provide vital cues for EC survival and proliferation through cell-surface integrin. Notably, biochemical analysis has shown that Ln, Fn, and Vn contain RGD (SEQ ID NO:36) sequences that can bind to cell surface integrin subunits to initiate cell attachment. In addition, the previous studies also demonstrate the amino acids surrounding the RGD (SEQ ID NO:36) peptide influence its activities. Based on this evidence, it was reasoned that there could be additional RGD-containing peptide segments derived from vascular endothelium ECM proteins (i.e., Ln, Fn and Vn) with higher affinity to EC integrin than the widely used RGDS (SEQ ID NO:35)/RGDSP (SEQ ID NO:34) peptides. The identification of these RGD (SEQ ID NO:36) peptides provides potent biological ligands for the development of vascularized tissue engineering constructs.

SUMMARY OF THE INVENTION

Embodiments of the present invention are directed to methods for identifying a compound that promotes endothelial cell adhesion, endothelial cell spreading, endothelial cell migration and/or endothelial cell proliferation for the manufacture of a diagnostic or therapeutic agent, including (a) contacting a hydrogel functionalized with at least one integrin-binding peptide with an endothelial cell integrin; and (b) determining the binding affinity of the integrin-binding peptide to the endothelial cell integrin, wherein a high binding affinity indicates that the integrin-binding peptide is a compound that promotes endothelial cell adhesion, endothelial cell spreading, endothelial cell migration and/or endothelial cell proliferation.

Embodiments of the present invention also provide assays for identifying a compound that promotes endothelial cell adhesion, endothelial cell spreading, endothelial cell migration and/or endothelial cell proliferation for manufacture of a diagnostic or therapeutic agent, the assay including screening a compound of interest for its binding effect on an endothelial cell integrin wherein the compound of interest is conjugated to a hydrogel and contacted to an endothelial cell integrin, wherein high affinity binding to the endothelial cell integrin indicates that the compound of interest promotes endothelial cell adhesion, endothelial cell spreading, endothelial cell migration and/or endothelial cell proliferation.

Embodiments of the present invention further provide peptides that bind an endothelial cell integrin as well as fragments and variants of the peptides that bind to an endothelial cell integrin when tested under the same test conditions as the parent peptide.

Embodiments of the present invention also provide a pharmaceutical composition including the peptides described herein and a pharmaceutically acceptable carrier, diluent, or excipient.

Embodiments of the present invention also provide methods of promoting angiogenesis.

Embodiments of the present invention further provide methods of promoting endothelial cell adhesion, endothelial cell spreading, endothelial cell migration and/or endothelial cell proliferation.

Embodiments of the present invention further provide methods of treating or preventing ischemic injury.

Embodiments of the present invention further provide methods of promoting tissue regeneration.

Embodiments of the present invention also provide a method for bioprinting and biomaterial products for bioprinting.

Embodiments of the present invention further provide kits including the elements necessary to carry out the processes described above.

BRIEF DESCRIPTION OF THE DRAWINGS

FIG. 7. The RGD (SEQ ID NO:36) peptide library used to screen high affinity ligands to endothelial cell integrins.

FIGS. 11A-D. HUVECs cultured in 3D alginate hydrogels functionalized with (A) α1 peptide and covalently bound QK, (B) RGDSP (SEQ ID NO:33) and MMP-responsive QK, (C) α1 peptide and MMP-responsive QK. (D) normalized total network length of (A)-(C). Blue-DAPI, Green-Phalloidin, scale bar is 25 μm.

DETAILED DESCRIPTION

Figure 1A:
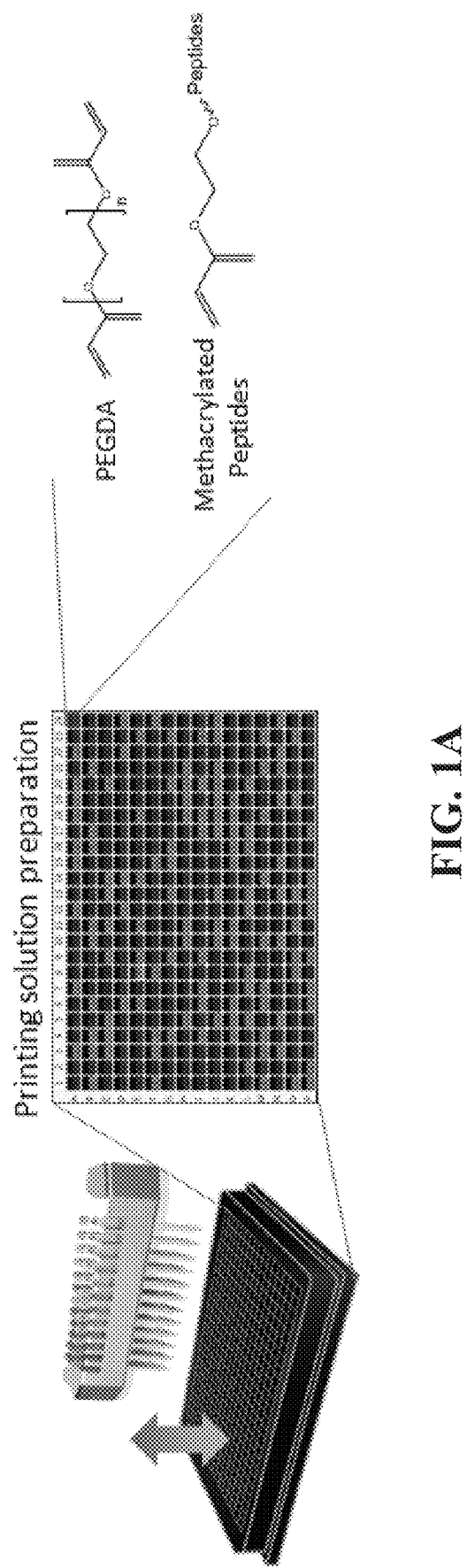
FIGS. 1A-C. Schematic representation of fabrication of peptide-functionalized PEG hydrogel microarrays. (A) The printing solutions composed of PEGDA monomer and various methacrylated peptides were prepared in a 384-well plate. (B) The printing solutions were placed onto poly (HEMA) coated microscope slides with a customized microarrayer and polymerized by UV under Argon protection to prepare peptide-functionalized PEG hydrogel spots. Eight hydrogel spots in a microarray were shown to present the dimension of the hydrogel spots and the distance between the hydrogel spots. (C) High throughput analysis of cellular activities after cell seeding onto the microarray.

The present invention is further described below in greater detail. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof. Further, all patent and patent application references referred to in this patent application are hereby incorporated by reference in their entirety as if set forth fully herein. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

As used herein, the transitional phrase "consisting essentially of" (and grammatical variants) means that the scope of a claim is to be interpreted to encompass the specified materials or steps recited in the claim, "and those that do not materially affect the basic and novel characteristic(s)" of the claimed invention. Thus, the term "consisting essentially of" when used in a claim of this invention is not intended to be interpreted to be equivalent to "comprising."

The term "endothelial" cells refer to simple squamous cells; a layer of which cells line the inside surfaces of body cavities, blood vessels, and lymph vessels. Endothelial cells provide a barrier between the blood and the rest of the body tissues. Other specialized functions of endothelial cells include producing nitric oxide (NO), blood vessel formation (angiogenesis), adhesion, spreading, migration and/or proliferation, blood clotting, inflammation, vasoconstriction, vasodilation, blood pressure and water regulation.

The term "arginine-glycine-aspartic acid" or "RGD" (SEQ ID NO:36) peptide refers to a peptide including the sequence L-arginine, glycine, and L-aspartic acid (RGD) (SEQ ID NO:36). The RGD (SEQ ID NO:36) sequence may function as the cell attachment site of a number of adhesive extracellular matrix, blood, and cell surface proteins, with various integrins recognizing the RGD (SEQ ID NO:36) sequence in their adhesion protein ligands.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, and/or synthesized chemically. Such techniques are known to those skilled in the art. See, e.g., Sambrook et al., *Molecular Cloning: A Laboratory Manual 2nd Ed* (Cold Spring Harbor, N.Y., 1989); Ausubel et al. Current Protocols in Molecular Biology (Green Publishing Associates, Inc. and John Wiley & Sons, Inc., New York).

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical, or substantially identical, to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. Moreover, as used herein, "portion" or "fragment" are used interchangeably and refers to less than the whole of the structure that substantially retains at least one biological activity normally associated with that molecule, protein or polypeptide. In particular embodiments, the "fragment" or "portion" substantially retains all of the activities possessed by the unmodified protein. By "substantially retains" biological activity, it is meant that the protein retains at least about 10%, 20%, 30%, 40%, 50%, 60%, 75%, 85%, 90%, 95%, 97%, 98%, 99%, or more, of the biological activity of the native protein (and can even have a higher level of activity than the native protein).

A fragment of a polypeptide or protein of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify biologically active fragments of the polypeptides described herein would be well within the scope of one of ordinary skill in the art and would be routine.

The term "variant" refers no more than one, two, three, four, five, six, seven, eight, nine or ten amino acid substitutions in the sequence of interest. The variant retains at least one biological activity normally associated with that amino acid sequence. In particular embodiments, the functional variant retains at least about 40%, 50%, 60%, 75%, 85%, 90%, 95% or more biological activity normally associated with the full-length amino acid sequence. In other embodiments, a functional variant is an amino acid sequence that is at least about 50%, 60%, 70%, 80%, 90%, 95% 97% or 98% similar to the peptide sequence disclosed herein (or fragments thereof).

As used herein, the terms "express," "expressing," or "expression" (or grammatical variants thereof) in reference to a gene or coding sequence can refer to transcription to produce an RNA and, optionally translation to produce a polypeptide. Thus, unless the context indicates otherwise, the terms "express," "expressing," "expression" and the like can refer to events at the transcriptional, post-transcriptional, translational and/or post-translational level.

"Posttranslational modification" has its usual and customary meaning and includes but is not limited to removal of leader sequence, γ-carboxylation of glutamic acid residues, β-hydroxylation of aspartic acid residues, N-linked glycosylation of asparagine residues, O-linked glycosylation of serine and/or threonine residues, sulfation of tyrosine residues, phosphorylation of serine residues and any combination thereof. Posttranslational modifications apply to the peptides described herein.

The term "isolated" can refer to a nucleic acid, polypeptide or cell that is substantially free of other cellular material, viral material, and/or culture medium (when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "extracellular matrix" or "ECM" protein refers to proteins found in the non-cellular macromolecular network providing physical scaffolding and biochemical support to surrounding cells. Exemplary ECM proteins include, but are not limited to, laminin (Ln), fibronectin (Fn), vitronectin (Vn), gelatin or collagen protein.

The term "integrin" refers to a cell-surface cellular adhesion molecule that can bind to ECM structures, such as the ECM proteins described herein.

The term "hydrogel" refers to a polymeric biomaterial having hydrophilic properties generally having water or a biological fluid as the continuous phase.

The term "biocompatible" refers to the condition of being not deleterious to living cells, tissues or organisms to the extent of not causing serious harm to the host, the host being a human or non-human host such as the subjects described herein.

The term "biomaterial product" refers to a biocompatible substance that has been engineered and is suitable to construct, replace, repair or augment cells, tissues and/or organs.

The term "angiogenesis" refers to the formation of new blood vessels derived from pre-existing blood vessels.

The terms "pro-angiogenic" or "angiogenic" growth factors (including all genes and isoforms of each gene product) for use in accordance with the methods of the present invention include, but are not limited to, vascular endothelial cell growth factor (VEGF), acidic fibroblast growth factor (aFGF), basic fibroblast growth factor (bFGF), epidermal growth factor, transforming growth factors α and β, platelet-derived endothelial growth factor, platelet-derived growth factor, tumor necrosis factor α, hepatocyte growth factor (scatter factor), erythropoietin, colony stimulating factor (CSF), macrophage-CSF (M-CSF), granulocyte/macrophage CSF (GM-CSF), angiopoietin 1 and 2, and nitric oxide synthase (NOS). The nucleic acid and amino acid sequences for these and other angiogenic growth factors are available in public databases such as GenBank and in the literature. Additionally, human VEGF 1 (VEGF A) exists in at least four principal isoforms, $VEGF_{121}$; $VEGF_{145}$; $VEGF_{165}$; and $VEGF_{189}$. There also exists VEGF 2 (also referred to as VEGF C); VEGF B; and VEGF D. Pro-angiogenic growth factors are further described below.

The terms "ischemic injury" or "ischemic disease" refer to diseases or disorders resulting from an insufficient supply of blood to an organ, often due to an occluded blood vessel. Examples of such include, but are not limited to, coronary artery disease, peripheral artery disease, ischemic wounds and diabetic ulcers.

The term "tissue regeneration" refers to the process of remodeling, renewal, growth, maintenance and/or improved function of cells, and in particular, cells collectively forming a tissue. The tissue may be tissue associated with the nervous system, endocrine system, hematopoietic system, gastrointestinal tract, renal system, cardiac system, vascular system, reproductive system, musculoskeletal system or combinations thereof. The tissue may be tissue associated with an organ such as the appendix, bladder, brain, ear, esophagus, eye, gall bladder, heart, kidney, large intestine, liver, lung, mouth, muscle, nose, ovary, pancreas, parathyroid gland, pineal gland, pituitary gland, skin, small intestine, spleen, stomach, testes, thymus, thyroid gland, trachea, uterus, vermiform appendix or combinations thereof. Tissue regeneration also includes wound healing.

"Bioprinting" or "3D bioprinting" refers to a process of creating cell patterns using 3D printing technologies with cell function, integrity and/or viability preserved during the printing process. Bioprinting usually employs a layer-by-layer method to create tissue-like structures that can be used in biomedical engineering and tissue regeneration and remodeling fields. Bioprinting can be used to print tissues and organs as well as scaffolds of the same.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the term "treat", "treating" or "treatment of" (and grammatical variations thereof) refer to a reduction in the amount and/or frequency of undesirable or uncontrolled bleeding.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing" or "prevention of" (and grammatical variations thereof) refer to prevention and/or delay of the onset and/or progression of undesirable or uncontrolled bleeding in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating an injury or disorder by the methods of the present invention can be determined by detecting a clinical improvement as indicated by a change in the subject's symptoms and/or clinical parameters as would be well known to one of skill in the art or in the improved properties of the cells and/or tissue as assessed by suitability for intended purposes of the present invention including, but not limited to, tissue regeneration, tissue transplants, wound healing, skin grafts, etc.

The present invention provides methods and biomaterials that can synergistically engage more than one type of endothelial cell integrins to promote endothelial cell adhesion, endothelial cell spreading, endothelial cell migration and/or endothelial cell proliferation further providing vascular network formation for therapeutic angiogenesis and/or vascular grafts.

The present invention also provides methods and biomaterials that synergistically engage endothelial cell integrins and pro-angiogenic growth factors to promote endothelial cell adhesion, endothelial cell spreading, endothelial cell migration and/or endothelial cell proliferation further providing vascular network formation for therapeutic angiogenesis and/or vascular grafts.

In some embodiments, the present invention provides an in vitro method for identifying a compound that promotes endothelial cell adhesion, endothelial cell spreading, endothelial cell migration and/or endothelial cell proliferation for the manufacture of a diagnostic or therapeutic agent, comprising, consisting of, or consisting essentially of: (a) contacting a hydrogel functionalized with at least one integrin-binding peptide with an endothelial cell integrin; and (b) determining the binding affinity of integrin-binding peptide to the endothelial cell integrin, wherein a high binding affinity indicates that the integrin-binding peptide is a compound that promotes endothelial cell adhesion, endothelial cell spreading, endothelial cell migration and/or endothelial cell proliferation. According to embodiments of the present invention, the number of attached cells on each of peptide-functionalized poly(ethylene glycol) (PEG) hydrogel spots is normalized to the number of attached cells on RGDS (SEQ ID NO:35) peptide functionalized PEG hydrogel spots. If the normalized cell binding is greater than 1, high affinity binding is achieved.

In some embodiments, the integrin-binding peptide is derived from at least one protein selected from the group consisting of laminin (Ln), fibronectin (Fn), vitronectin (Vn), collagen, fibrinogen, von Willebrand factor, thrombospondin, laminin, entactin, tenascin, osteopontin, bone sialoprotein, and subunits thereof. In some embodiments, the laminin subunit is laminin subunit α1. In some embodiments, the integrin-binding peptide is an arginine-glycine-aspartic acid (RGD) (SEQ ID NO:36) peptide.

In some embodiments, a hydrogel of the present invention includes agarose, polyethylene glycol, alginate, hyaluronic acid, polyacryylic acid, polyacrylic amide, polyvinyl alcohol, polyhydroxyethyl methacrylate, methacrylated dextrans, poly(N-isopropylacrylamide), or any combination thereof. In some embodiments, the hydrogel includes polyethylene glycol.

In some embodiments, the hydrogel is functionalized (e.g., coupled) with more than one integrin-binding peptide, wherein the integrin-binding peptide is the same type of integrin-binding peptide or at least one of the integrin-binding peptides is different from one other integrin-binding peptide. Functionalization of hydrogels with peptides includes conjugation of peptides to hydrogels through covalent and/or non-covalent bonding. As shown in the examples, covalent conjugation of peptides onto hydrogels has been accomplished using at least three different chemistries: 1) co-polymerized methacrylated peptides with poly(ethylene glycol) diacrylates, 2) EDC-NHS chemistry to conjugate peptides to alginate hydrogel, and 3) click chemistry to conjugate peptides to alginate hydrogel. In particular embodiments, the hydrogel is functionalized to an integrin-binding peptide that binds to αvβ3 integrin. In some embodiments, the integrin-binding peptide binds to VLA-6 integrin. In some embodiments, the integrin-binding peptide binds to both αvβ3 and VLA-6 integrin.

In some embodiments, the identified compound promotes endothelial cell adhesion, endothelial cell spreading, endothelial cell migration and/or endothelial cell proliferation by modulating the activity of vascular endothelial growth factor receptor 2 (VEGFR2). In yet some embodiments, the compound modulates the activity of VEGFR2 by up-regulating VEGFR2 mRNA expression. As used herein, "modulate," "modulates" or "modulation" refers to enhancement (e.g., an increase) or inhibition (e.g., a reduction) in the specified activity.

Embodiments of the present invention also provide assays for identifying a compound that promotes endothelial cell adhesion, endothelial cell spreading, endothelial cell migration and/or endothelial cell proliferation for manufacture of a diagnostic or therapeutic agent, the assay comprising, consisting essentially of, or consisting of screening a compound of interest for its binding effect on an endothelial cell integrin wherein the compound of interest is conjugated to a hydrogel and contacted to an endothelial cell integrin, wherein high affinity binding to the endothelial cell integrin indicates that the compound of interest promotes endothelial cell adhesion, endothelial cell spreading, endothelial cell migration and/or endothelial cell proliferation. In some embodiments the assay is a microarray. "Microarray" as used herein refers to a large collection of miniaturized peptide-functionalized hydrogel spots placed onto two-dimensional substrates (e.g., glass slides) in a spatially numbered matrix.

In some embodiments, the endothelial cell integrin is derived from an endothelial cell that includes endothelial cells derived from stem cells, progenitor cells, and different organs (such as the appendix, bladder, brain, ear, esophagus, eye, gall bladder, heart, kidney, large intestine, liver, lung, mouth, muscle, nose, ovary, pancreas, parathyroid gland, pineal gland, pituitary gland, skin, small intestine, spleen, stomach, testes, thymus, thyroid gland, trachea, uterus, or vermiform appendix) and from different species including mouse, rat, rabbit, sheep, goat and human. In some embodiments, the endothelial cell is a human umbilical vein endothelial cell (HUVEC), a human induced pluripotent stem cell-derived endothelial cell (hiPSC-EC), a human endothelial progenitor cell (hEPC), a human microvascular endothelial cell (hMEC), and combinations thereof. The endothelial cell integrins may be derived from or included in a sample including the cell types described herein. In particular embodiments, the endothelial cell integrin is derived from a human umbilical vein endothelial cell (HUVEC).

Embodiments of the present invention also provide peptides that bind to an endothelial cell integrin, the peptide selected from the group comprising, consisting essentially of, or consisting of the following sequences: TFALRGDNP (SEQ ID NO:1) (derived from Laminin subunit α1); TFALRADNP (SEQ ID NO:2); DVEKRGDREEAHVP (SEQ ID NO:3) (derived from Laminin subunit α1); IQRGDIDAMIS (SEQ ID NO:4) (derived from Laminin subunit α3); DAVKQLQAAERGDA (SEQ ID NO:5) (derived from Laminin subunit α4); PMQKMRGDVFSP (SEQ ID NO:6) (derived from Laminin subunit β4); RSDGTG (SEQ ID NO:7) (derived from Laminin subunit γ2); and EAPRGDVYQG (SEQ ID NO:8) (derived from Laminin subunit γ3), and fragments and variants thereof that bind to an endothelial cell integrin when tested under the same test conditions as the parent peptide including non-naturally occurring and/or modified peptides.

Embodiments of the present invention also provide pharmaceutical compositions comprising, consisting essentially of or consisting of a peptide described herein, and a pharmaceutically acceptable carrier, diluent, or excipient. The particular choice of carrier, diluent, or excipient and formulation will depend upon the particular route of administration for which the composition is intended.

The pharmaceutical compositions of the present invention may be suitable for parenteral, oral, inhalation spray, topical, rectal, nasal, buccal, vaginal or implanted reservoir administration, etc. The term "parenteral" as used herein includes subcutaneous, intradermal, intravenous, intramuscular, intra-articular, intra-synovial, intrasternal, intrathecal, intrahepatic, intralesional, intraarterial, intramyocardial and intracranial injection or infusion techniques.

Where the compounds described herein are to be applied in the form of solutions or injections, the compounds may be used by dissolving or suspending in any conventional diluent. The diluents may include, for example, physiological saline, Ringer's solution, an aqueous glucose solution, an aqueous dextrose solution, an alcohol, a fatty acid ester, glycerol, a glycol, an oil derived from plant or animal sources, a paraffin and the like. These preparations may be prepared according to any conventional method known to those skilled in the art.

Embodiments of the present invention further provide hydrogel compositions comprising, consisting essentially of, or consisting of (a) at least one integrin-binding peptide selected from the group comprising, consisting essentially of, or consisting of the following sequences: TFALRGDNP (SEQ ID NO:1) (derived from Laminin subunit α1); DVEKRGDREEAHVP (SEQ ID NO:3) (derived from Laminin subunit α1); IQRGDIDAMIS (SEQ ID NO:4) (derived from Laminin subunit α3); DAVKQLQAAERGDA (SEQ ID NO:5) (derived from Laminin subunit α4); PMQKMRGDVFSP (SEQ ID NO:6) (derived from Laminin subunit β4); RSDGTG (SEQ ID NO:7) (derived from Laminin subunit γ2); and EAPRGDVYQG (SEQ ID NO:8) (derived from Laminin subunit γ3), and fragments and variants thereof that bind to an endothelial cell integrin when tested under the same test conditions as the parent peptide and (b) a biocompatible polymer, wherein the integrin-binding peptide is linked to the biocompatible polymer.

Embodiments of the present invention also provide hydrogel compositions comprising, consisting essentially of, or consisting of (a) at least one integrin-binding peptide selected from the group comprising, consisting essentially of, or consisting of the following sequences: TFALRGDNP (SEQ ID NO:1) (derived from Laminin subunit α1); DVEKRGDREEAHVP (SEQ ID NO:3) (derived from Laminin subunit α1); IQRGDIDAMIS (SEQ ID NO:4) (derived from Laminin subunit α3); DAVKQLQAAERGDA (SEQ ID NO:5) (derived from Laminin subunit α4); PMQKMRGDVFSP (SEQ ID NO:6) (derived from Laminin subunit β4); RSDGTG (SEQ ID NO:7) (derived from Laminin subunit γ2); and EAPRGDVYQG (SEQ ID NO:8) (derived from Laminin subunit γ3), and fragments and variants thereof that bind to an endothelial cell integrin when tested under the same test conditions as the parent peptide and/or at least one integrin-binding peptide selected from the group consisting of GLOGERGRO (SEQ ID NO:9), GFOGERGVQ (SEQ ID NO:10), DGEA (SEQ ID NO: 1), GFOGER (SEQ ID NO:12), GLKGEN (SEQ ID NO:13), LDV (SEQ ID NO:14), REDV (SEQ ID NO:15), PEDGIHE (SEQ ID NO:16), PHSRN (SEQ ID NO:17), ALNGR (SEQ ID NO:18), IAFQRN (SEQ ID NO:19), IKLLI (SEQ ID NO:20), SIKVAV (SEQ ID NO:21), AGQWHRVSVRWG (SEQ ID NO:22), TWSQKALHHRVP (SEQ ID NO:23), SIYITRF (SEQ ID NO:24), SYWYRIEASRTG (SEQ ID NO:25), YIGSR (SEQ ID NO:26), RDIAEIIKDI (SEQ ID NO:27), VFDNFVLK (SEQ ID NO:28), AEIDGIEL (SEQ ID NO:29), SETQRGDVFVP (SEQ ID NO:30), PASYRGDSC (SEQ ID NO:31), VTGRGDSPAS (SEQ ID NO:32), RGDSP (SEQ ID NO:33), RGDS (SEQ ID NO:35), RGD (SEQ ID NO:36), PQVTRGDVFTMP (SEQ ID NO:37), and fragments and variants thereof; (b) pro-angiogenic growth factors that include, but are not limited to, VEGF (vascular endothelial growth factor); Ang2 (angiopoietin 2); PDGF (platelet-derived growth factor); PLGF (placenta growth factor); SDF-1 (stromal cell-derived factor-1); FGF (fibroblast growth factor); Ang1 (angiopoietin 1) and fragments and variants thereof, and the fragments and variants of pro-angiogenic growth factors, which include pro-angiogenic growth-factor mimetic peptides that include, but are not limited to, VEGF mimetic peptide (KLTWQELYQLKYKGI, SEQ ID NO:38); PDGF mimetic peptide (C*VRKIEIVRKK)2-Ahx-Ahx-Ahx-RKRKLERIAR-NH2) (SEQ ID NO:39); Ang 1 mimetic peptide (PEG-CHHHRHSF, SEQ ID NO:40) tetramer); and/or a pro-angiogenic growth factor binding compound that include, but are not limited to, heparin, heparin-binding peptide; and (c) a biocompatible polymer, wherein the integrin-binding peptide and/or the pro-angiogenic growth factors and fragments and variants thereof are linked to the biocompatible polymer.

In some embodiments, the hydrogel compositions include covalent or non-covalent linkages. In some embodiments, the biocompatible polymer of the hydrogel is functionalized with VEGF mimetic peptide (KLTWQELYQLKYKGI, SEQ ID NO:38) and an integrin-binding peptide that binds at least one type of endothelial cell integrin. In some embodiments, the VEGF mimetic peptide is attached to the biocompatible polymer through a matrix metalloproteinase (MMP) degradable peptide linkage (for example, GPQG↓IAGKLTWQELYQLKYKGI (SEQ ID NO:41), PES↓LRAG (SEQ ID NO:42), GPQG↓IWGQ (SEQ ID NO:43), VPLS↓LYSG (SEQ ID NO:44)). In some embodiments, the biocompatible polymer of the hydrogel composition is functionalized with a VEGF mimetic peptide and an integrin binding peptide that binds to an $\alpha_v\beta_3$ integrin. In some embodiments, the biocompatible polymer of the hydrogel composition is functionalized with a VEGF mimetic peptide and an integrin binding peptide that binds to a VLA-6 integrin. In some embodiments, the biocompatible polymer of the hydrogel composition is functionalized with a VEGF mimetic peptide and an integrin binding peptide that binds to an $\alpha_v\beta_3$ integrin and a VLA-6 integrin. In some embodiments, the biocompatible polymer of the hydrogel composition is functionalized with an integrin binding peptide that binds to an $\alpha_v\beta_3$ integrin and a VLA-6 integrin.

In some embodiments, the biocompatible polymer comprises, consists essentially of, consists of agarose, polyethylene glycol, alginate, hyaluronic acid, polyacrylic acid, polyacrylic amide, polyvinyl alcohol, polyhydroxyethyl methacrylate, methacrylated dextrans, poly(N-isopropylacrylamide), or any combination thereof. In particular embodiments, the biocompatible polymer is 5% oxidized alginate.

In particular embodiments, the hydrogel composition is an injectable and/or extrudable composition. In some embodiments, the injectable hydrogel may be 1% w/w alginates with 5% oxidation. In some embodiments, the extrudable hydrogel is applicable for bioprinting. In some embodiments, the extrudable hydrogel for bioprinting may be 1% w/w alginates with 5% oxidation.

Embodiments of the present invention further provide methods of promoting angiogenesis in a subject in need thereof comprising, consisting essentially of or consisting of administering to the subject a peptide described herein, a pharmaceutical composition described herein, a hydrogel composition described herein and/or a biomaterial product described herein, in an amount effective to promote angiogenesis.

Embodiments of the present invention provide methods of promoting endothelial cell adhesion, endothelial cell spreading, endothelial cell migration and/or endothelial cell proliferation comprising, consisting essentially of or consisting of administering a peptide described herein, a pharmaceutical composition described herein, a hydrogel composition described herein and/or a biomaterial product described herein in an amount effective to promote endothelial cell adhesion, endothelial cell spreading, endothelial cell migration and/or endothelial cell proliferation.

Embodiments of the present invention provide methods of treating or preventing ischemic injury in a subject in need thereof comprising, consisting essentially of or consisting of administering to the subject a peptide described herein, a pharmaceutical composition described herein, a hydrogel composition and/or a biomaterial product described herein, in an amount effective to treat or prevent ischemic injury. The ischemic injury or ischemic disease refers to diseases or disorders resulting from an insufficient supply of blood to an organ, often due to an occluded blood vessel. Examples of such include, but are not limited to, coronary artery disease, peripheral artery disease, ischemic wounds and diabetic ulcers.

Embodiments of the present invention also provide methods of promoting tissue regeneration in a subject in need thereof comprising, consisting essentially of or consisting of administering to the subject a peptide described herein, a pharmaceutical composition described herein and/or a hydrogel composition described herein, in an amount effective to promote tissue regeneration. The tissue regeneration refers to the process of remodeling, renewal, growth, maintenance and/or improved function of cells, and in particular, cells collectively forming a tissue. The tissue may be tissue associated with the nervous system, endocrine system, hematopoietic system, gastrointestinal tract, renal system, cardiac system, vascular system, reproductive system, musculoskeletal system or combinations thereof. The tissue may be tissue associate with an organ such as the appendix, bladder, brain, ear, esophagus, eye, gall bladder, heart, kidney, large intestine, liver, lung, mouth, muscle, nose, ovary, pancreas, parathyroid gland, pineal gland, pituitary gland, skin, small intestine, spleen, stomach, testes, thymus, thyroid gland, trachea, uterus, vermiform appendix or combinations thereof. Tissue regeneration also includes wound healing.

The subjects to be treated according to the present invention include any subject in whom promotion of angiogenesis, prevention and/or treatment of ischemic injury and/or tissue regeneration is desired or needed, as well as any subject prone to such. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., including domesticated animals, companion animals and wild animals for veterinary medicine or treatment or pharmaceutical drug development or biomedical research purposes.

The subjects relevant to this invention may be male or female and may be any species and of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric.

Embodiments of the present invention also provide kits including the elements necessary to carry out the processes described above. Such a kit may comprise a carrier being compartmentalized to receive in close confinement therein one or more containers, such as tubes or vials. One or more of the containers may contain a peptide or composition described herein. One or more containers may contain one or more enzymes or reagents to be utilized in desired reactions. These enzymes may be present by themselves or in admixtures, in lyophilized form or in appropriate buffers. The kit may contain all of the additional elements necessary to carry out techniques of the invention, such as buffers, control plasmid, oligonucleotides, extraction reagents, fixation agents, permeability agents, enzymes, pipettes, plates, nucleic acids, gel materials, transfer materials, autoradiography supplies, instructions and the like. In particular, embodiments of the present invention provide kits comprising, consisting essentially of or consisting of a peptide described herein, a pharmaceutical composition described herein, a hydrogel composition described herein and/or a biomaterial product described herein, and a container suitable for delivery of the peptide, pharmaceutical composition or hydrogel composition into an administration device, with optional instructions for the use thereof. In some embodiments, the administration device is a parenteral administration device. In some embodiments, the administration device is an intramyocardial device. In some embodiments, the kit is not limited by size and includes a biomaterial product and/or a bioprinter.

The general procedure for implementing the methods and assays of the present invention can be readily understood and appreciated by one skilled in the art. Some aspects of the present invention are described in more detail in the following non-limiting Examples. These are not intended to restrict the present invention, and may be modified within the range not deviating from the scope of this invention.

EXAMPLES

Example 1: Development of Peptide-Functionalized Synthetic Hydrogel Microarrays for Stem Cell and Tissue Engineering Applications This experimental section describes the development of a platform technology based on light-assisted co-polymerization of poly(ethylene glycol) diacrylates (PEGDA) and methacrylated-peptides to fabricate peptide-functionalized hydrogel microarrays. To this end, the high efficiency of solid-phase peptide synthesis and isocyanation chemistry was leveraged to develop a robust synthetic route for preparing methacrylated-peptides. Due to their high solubility in DMF and high miscibility with low molecular PEGDA, methacrylated-peptides can be effectively incorporated into PEG hydrogels in a ratiometric and homogenous manner. In addition, several parameters were optimized, including the length of the linker between methacrylate functional groups and cell-binding peptide moieties to ensure high accessibility of the peptide functional groups to the cell-surface receptors. To apply the peptide-functionalized hydrogel technology, we constructed a library composed of 12 different RGD (SEQ ID NO:36) peptides to develop synthetic culture substrates for human induced pluripotent stem cell-derived cardiomyocytes (hiPSC-CMs), a cell type known for poor adhesion to synthetic substrates. While 6 of the 12 peptides were found through reported literature, bioinformatic screening of ECM proteins led to the identification of 6 unexplored RGD (SEQ ID NO:36) peptides. Notably, 2 out of 6 unexplored RGD (SEQ ID NO:36) peptides showed substantial affinity to hiPSC-CMs. One of them, PMQKMRGDVFSP (SEQ ID NO:6) from laminin β4 subunit, was found to have the highest affinity to hiPSC-CMs. With the support of bioinformatic screening, peptide-functionalized hydrogel microarrays are shown here to be a promising strategy to rapidly identify novel biological ligands for the development of functional biomaterials for stem cell and tissue engineering applications.

Materials and Instruments.

All chemicals used for this study were purchased from Sigma-Aldrich (St. Louis, Mo.) unless otherwise stated. Microarray spotting pins (946MP9B) were purchased from Arrayit Corporation (Sunnyvale, Calif.). A custom designed microarrayer was assembled and produced by BioDot (Irvine, Calif.). The liquid chromatography-mass spectrometer (LC-MS) system used is Thermo Fisher LCQ Fleet™ Ion Trap Mass Spectrometer.

Bioinformatics-Assisted ECM Protein Screening.

Bioinformatics-assisted ECM protein screening for highly conserved sequences was performed using the following database: UniProt database, which is supported by European Bioinformatics Institute (EMBI-EBI), the SIB Swiss Institute of Bioinformatics, and the Protein Information Resource (PIR). The specific sequence of each ECM protein/ECM protein subunit was collected from mammalian species, including human, mouse, rat, chimpanzee, horse, sheep, rabbit, bovine, guinea pig, cat and dog. The protein alignment was achieved by using the tool of Clustal Omega from EMBL-EBI. The algorithm is described by J. Söding.

Monomer Preparation and Array Fabrication

Synthesis and Characterization of Methacrylated Peptides.

Peptides used in this work were synthesized by solid phase peptide synthesis (SPPS). The SPPS was conducted using the standard procedure described in Novabiochem peptide synthesis manual. To prepare methyacrylated peptides, 2-isocyanatoethyl methacrylate (3 equivalent (eq) dissolved in DMF) was used to react with the terminal amine group of the peptide chain (1 eq) before they were cleaved from the resin. This solid-phase isocyanation chemistry was first reported by Lee Ayres et al. All the methacrylated peptides prepared in this study were purified by using a Combiflash® purification system (RediSep Rf) in Reversed Phase format using C18 Columns (Teledyne Isco, Lincoln, Nebr.) running a solvent gradient from 100% $H_2O$ to 100% acetonitrile in 15~20 minutes. The peptides were eluted from the column at approximately 70% acetonitrile/30% $H_2O$. The purified peptides were subsequently characterized by LC-MS.

Microarray Fabrication.

Methacrylated peptides were dissolved in DMF at pre-designated ratios and mixed with PEGDA (containing 1% DMPA as initiator) (DMF solution of methacrylated peptide: PEGDA=1:1 (v/v)) and then transferred into a 384 well plate for microarray fabrication. The microarrays were printed in a humid Ar-atmosphere on epoxy monolayer-coated glass slides (Xenopore XENOSLIDE E, Hawthorne, N.J.) that were first dip-coated in 4 v/v % poly(hydroxyethyl methacrylate) (i.e., poly(HEMA)) using a customized microarrayer (Biodot). Spots were polymerized via 10 s exposure to long wave UV using a XX-15L UV bench lamp (365 nm) (UVP LLC, Upland, Calif.), dried at <50 mtorr for at least 7 days. Before use, the chips were sterilized by UV for 30 min for each side, and then washed with PBS twice for 15 min to remove residual monomer or solvent. Additional information to prepare the microarrays for different applications is provided below.

PEGDA Selection.

Figure 3:
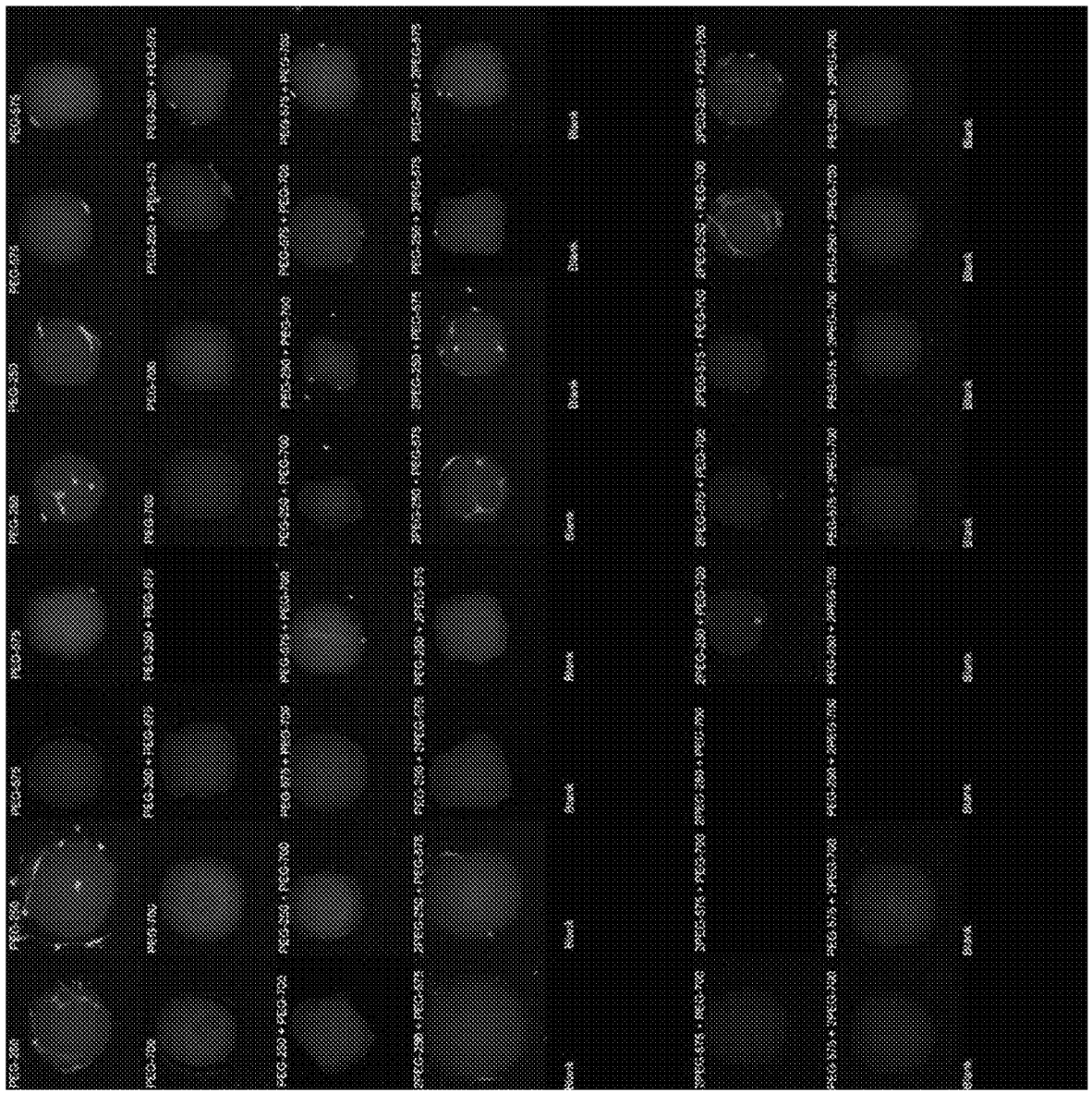
FIG. 3. hADSCs were seeded onto an 8×8 hydrogel microarray prepared from PEGDA-250, PEGDA-575, or PEGDA-700 to identify suitable formulations to inhibit unspecific cell adhesion.

Three commercially available PEGDA (M. W.=250, 575, 700) were selected and mixed at the designated ratios to produce the hydrogel microarrays (FIG. 3). To determine their abilities to inhibit unspecific cell adhesion, human adipose-derived stem cells (hADSCs) were seeded on the array and cultured for 12 hours. They were then fixed and stained with DAPI (1:1000 in DPBS) for cell number counting and phalloidin (1:200 in DPBS) for F-actin to estimate cell spreading.

The Effects of Glycine Linker Length.

Figures 5A, 5B:
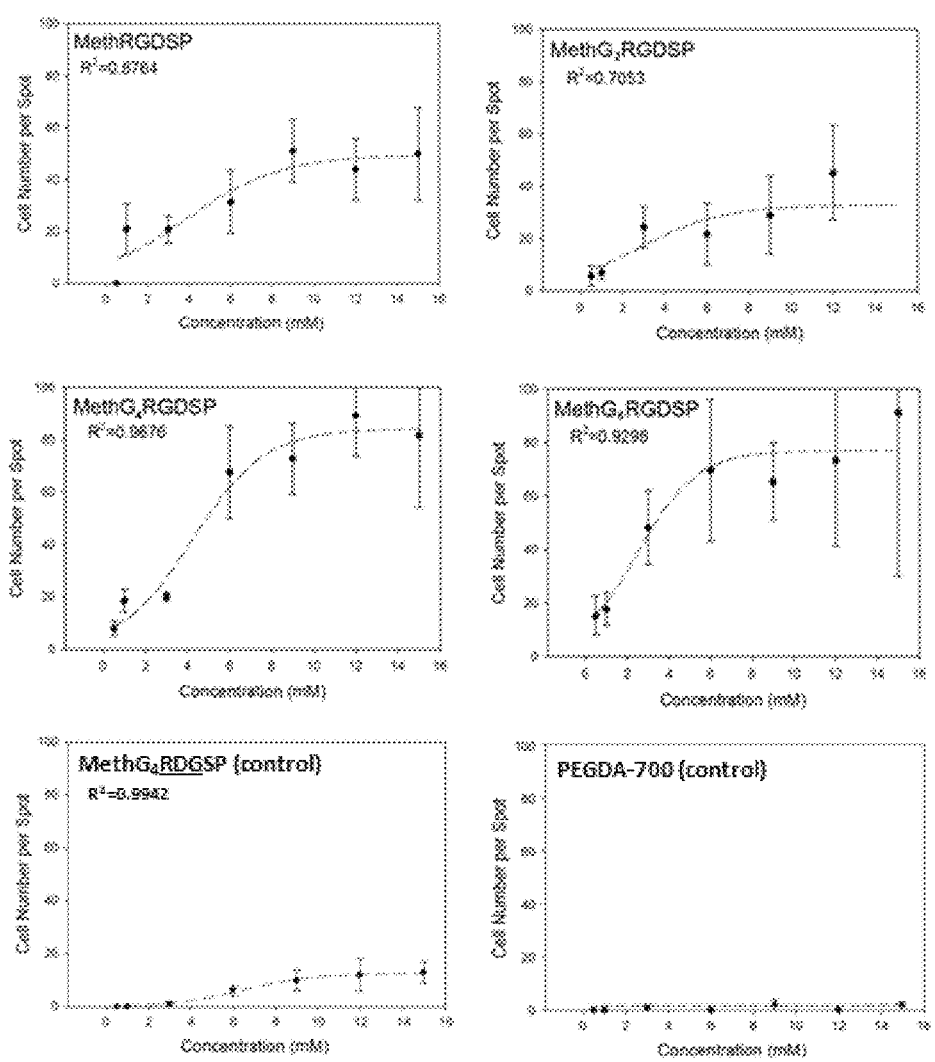
FIGS. 5A-C. Selection of a suitable linker to ensure the exposure of peptide moieties on PEG hydrogel surface. (A) A list of peptides used for the linker selection: RGDSP (SEQ ID NO:33) peptides fused with zero/two/four/six glycine linker, RDGSP (SEQ ID NO:34) and no peptide functionalization (blank PEGDA-700 hydrogel) have been employed as controls. (B) Effects of peptide concentration on the average number of the attached hADSCs on the hydrogel spots and the sigmoidal curve-fits. (C) Effects of glycine linker length on the saturated number of attached hADSCs on the hydrogel spots. All values are mean+SD. Asterisk denotes significant difference between blank PEGDA-700 hydrogels, MethG$_4$RDGSP (SEQ ID NO:47) and MethRGDSP (SEQ ID NO:33), MethG$_2$RGDSP (SEQ ID NO:45). Double asterisk denotes significant difference between MethRGDSP (SEQ ID NO:33), MethG$_2$RGDSP (SEQ ID NO:45) and MethG$_4$RGDSP (SEQ ID NO:46), MethG$_6$RGDSP (SEQ ID NO:48).

The methacrylated peptides used in these experiments are shown in FIG. 5A. PEGDA and methacrylated peptides were mixed at varied peptide concentrations (i.e., 0.5, 1, 3, 6, 9, 12 and 15 mM) to prepare microarrayed hydrogels with different peptide concentrations. hADSCs were seeded onto the array and cultured for 12 hours. They were then fixed and stained with DAPI (1:1000 in DPBS) for cell number counting and phalloidin (1:200 in DPBS) for F-actin to estimate cell spreading.

Screening RGD Peptides for hiPSC-CM Adhesion and Quantification of Sarcomere Formation.

Figure 6A:
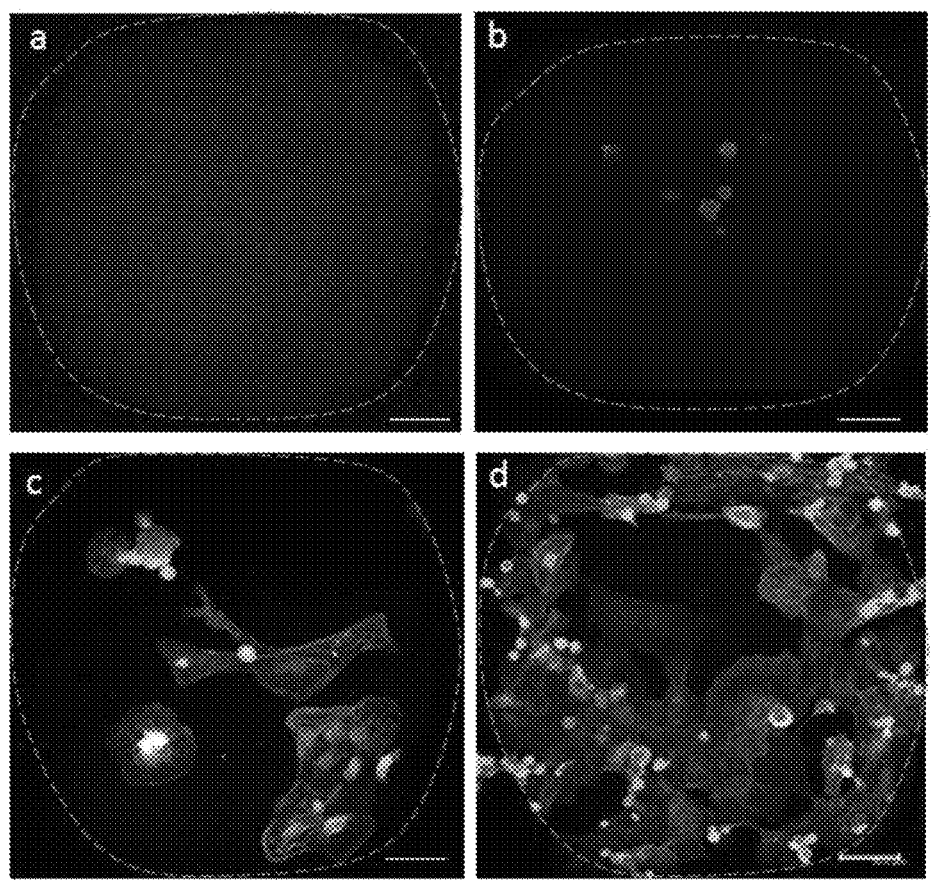
FIGS. 6A-E. hiPSC-CM adhesion and sarcomere formation on hydrogel microarrays. (A) The representative pictures of hiPSC-CMs on PEG hydrogel spots functionalized with different RGD (SEQ ID NO:36) peptides (blue: DAPI; green: sarcomere actinin; red: Troponin-I, scale bar=50 μm): (a) PEG hydrogel spots functionalized with RGD (SEQ ID NO:36) peptides that could not support adhesion of hiPSC-CMs. (b) PEG hydrogel spots functionalized with peptides that can support minimal cell adhesion. (c) PEG hydrogel spots functionalized with peptides that can moderately support cell adhesion (d) PEG hydrogel spots functionalized with RGD (SEQ ID NO:36) peptides that can effectively promote hiPSC-CM adhesion and sarcomere formation, a critical step for cardiomyocyte maturation. (B) A list of RGD (SEQ ID NO:36) peptides used in this experiment and their molecular origin. (C) The average number of attached hiPSC-CMs on the hydrogel spots functionalized with RGD (SEQ ID NO:36) peptides from laminin β4 chain, RGD (SEQ ID NO:36) peptides from Vn and two controls (i.e., blank PEGDA-700 hydrogel and RDGSP (SEQ ID NO:34) peptide functionalized hydrogel). All values are mean+SD. Asterisk denotes significant difference between RGD (SEQ ID NO:36) peptide from laminin β4 chain, RGD (SEQ ID NO:36) peptide from Vn and two control groups. Double asterisk denotes significant difference between laminin β4 RGD (SEQ ID NO:36) peptides and Vn RGD (SEQ ID NO:36) peptide. (D) The average number of attached hiPSC-CMs on PEG hydrogel spots functionalized with all different RGD (SEQ ID NO:36) sequences. Asterisk denotes significant difference between the "active" RGD (SEQ ID NO:36) peptides and "inactive" RGD (SEQ ID NO:36) peptides plus two control groups. Double asterisk denotes significant difference between laminin β4 RGD (SEQ ID NO:36) peptides, RGDSP (SEQ ID NO:33) and other RGD (SEQ ID NO:36) peptides from ECM proteins. Peptides labeled with asterisk were identified through bioinformatics screening. (E) The sarcomere actinin expressions of hiPSC-CMs (pixels per cell) cultured on the hydrogel spots. Asterisk denotes significant difference between RGD (SEQ ID NO:36) peptide from laminin β4 chain and RGD (SEQ ID NO:36) peptides from Vn, Fn, α5-2, α4. Peptides labeled with asterisk were identified through bioinformatics screening.
Figures 6B, 6C:
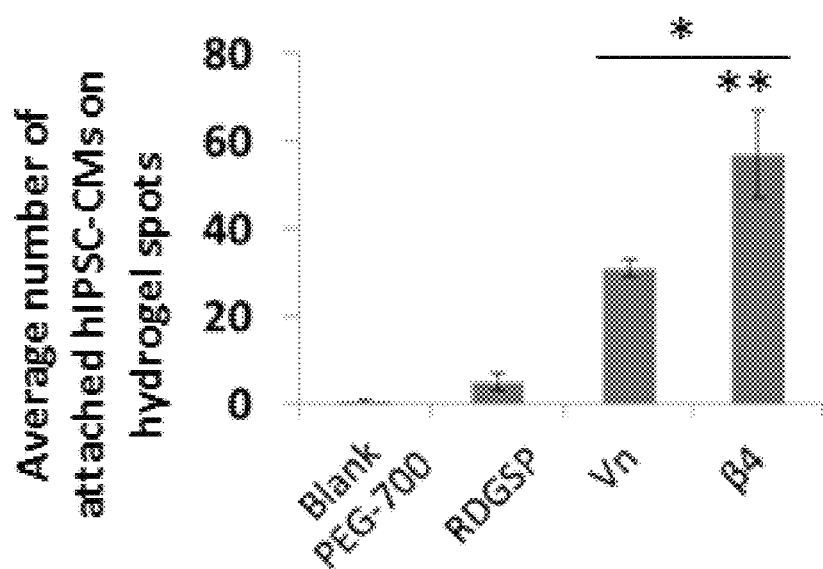
Figure 6D:
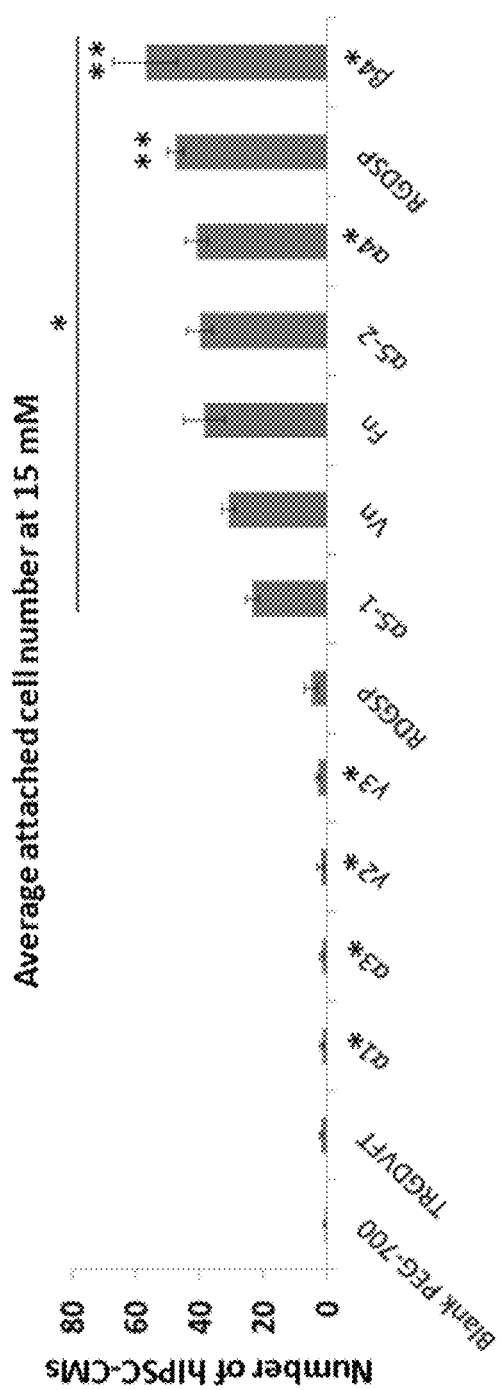
Figure 6E:
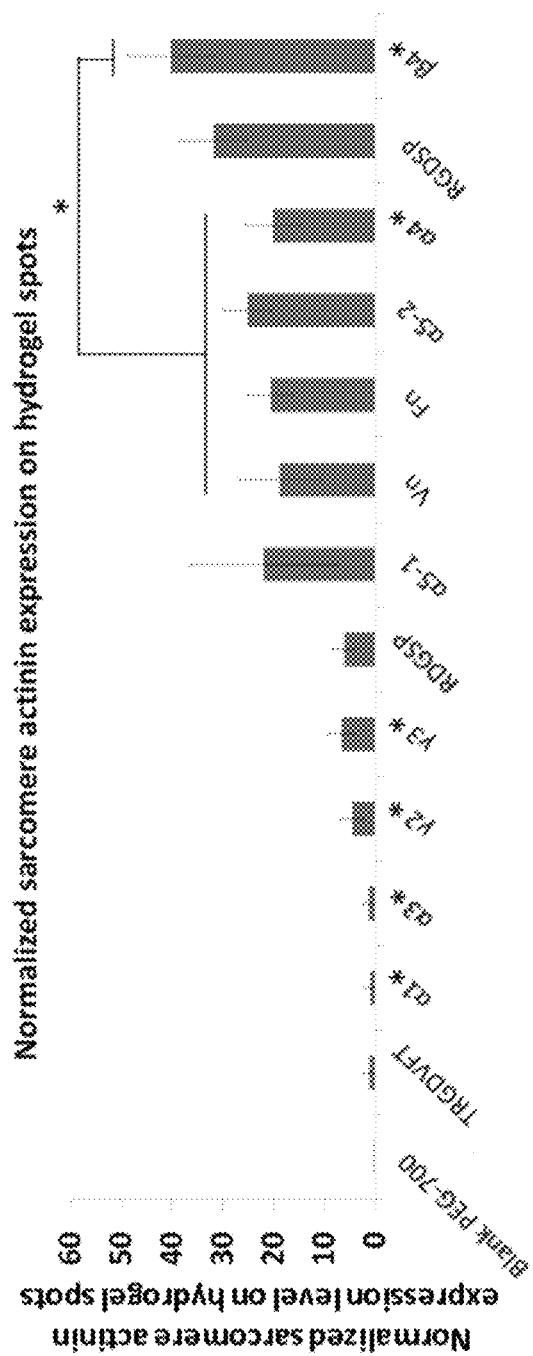

The methacrylate peptides used in this experiment are shown in FIG. 6B. PEGDA and methacrylated peptides were mixed at one fixed peptide concentration (15 mM) to prepare microarrayed hydrogels with a constant peptide concentration. hiPSC-CMs (human induced pluripotent stem cell-derived cardiomyocytes from Cellular Dynamics International, Madison, Wis., USA) were seeded onto the microarray and cultured for 3 days to facilitate the formation of sarcomere structures. hiPSC-CMs were stained with DAPI to approximate cell number and phalloidin for F-actin to estimate cell spreading. Sarcomere structure was examined by using immunofluorescence microscopy.

Briefly, hiPSC-CMs on the microarray were fixed with 4% PFA solution and blocked by 10% goat serum. After incubated with mouse anti-alpha sarcomeric actinin antibody (Abcam, Cambridge, UK) and rabbit anti-troponin I antibody (Santa Cruz, Dallas, Tex.) at a dilution ratio of 1:200 in PBS (with 0.1% Triton-100×) at room temperature for 1 hr, the microarrays were stained with the secondary antibodies (Alexa-488 goat anti-mouse IgG and Alexa-647 goat anti-rabbit IgG) at a dilution ratio of 1:200 in PBS (with 0.1% Triton-100×). Subsequently, the microarrays are stained with DAPI (1:1000 in DPBS) for nuclear counting. The fluorescently stained microarrays were imaged with a TCS SP5 AOBS laser scanning confocal microscope (Leica Microsystems, Inc., Exton, Pa.). Z-stacked Images collected from the microarray were analyzed by using the ImageJ (National Institutes of Health) for semi-quantitative analysis of the expression level of alpha sarcomeric actinin of hiPSC-CMs on the microarrays. The sarcomeric actinin expression level of hiPSC-CMs on each hydrogel spot was determined by the total fluorescence intensities of sarcomeric actinin staining divided by the total cell number on the hydrogel spot, which was then normalized to the blank PEG-700 hydrogel spots. The fluorescence intensities of sarcomeric actinin staining on each hydrogel spot were obtained by taking the sum of the green (sarcomeric actinin staining) pixels (i.e., fluorescence area coverage) through the total thickness of the Z-stacked images.

Cell Culture hADSC Culture.

hADSCs (Lonza, Basel, Switzerland) were used to study cell attachment for the hydrogel array. The cells were cultured in low glucose Dulbecco's modified Eagle's medium with 10% fetal bovine serum and 1% penicillin-streptomycin, 1% glutamine and 1% antimycin (Gibco Life Technologies, Grand Island, N.Y.). At >80% confluency, cells were detached using trypLE Express (Gibco Life Technologies) and passaged. All experiments were conducted using passage 5 (P5) hADSCs. The cells were seeded along with culture media onto the hydrogel microarrays. After 12 hours culture, the cells were fixed and stained to examine the cell attachments on each spot hADSCs were stained with DAPI (1:1000 in DPBS) in order to approximate cell number. Cell spreading was visualized using phalloidin (1:200 in DPBS) staining.

hiPSC-CMs Culture.

hiPSC-derived cardiomyocytes (iCell Cardiomyocytes, Cellular Dynamics International, Madison, Wis., USA) were cultured according to the manufacturer's protocol. Briefly, hiPSC-derived cardiomyocytes were plated on 0.1% gelatin coated 6-well plates in iCell Cardiomyocytes Plating Medium (Cellular Dynamics International) at a density of about $3 \times 10^5$ to $4.0 \times 10^5$ cells/well and incubated at 37° C. in 5% $CO_2$ for 4 days. Two days after plating, the plating medium was removed and replaced with 4 mL of iCell Cardiomyocytes Maintenance Medium (Cellular Dynamics International). After 4 days of monolayer pre-culture, cells were detached using trypLE Express (Gibco Life Technologies, Grand Island, N.Y.) and seeded along with culture media on the hydrogel microarrays. Cells were culture for 3 days to allow the hiPSC-CMs to develop sarcomere structures. hiPSC-CMs were stained with DAPI (1:1000 in DPBS) to approximate cell attachment number and phalloidin (1:200 in DPBS) for F-actin to estimate cell spreading. Sarcomere structures were visualized using sarcomere actinin and troponin-I staining as described above.

Statistical Analysis

The results were shown in the mean+standard derivation (SD) and analyzed using Sigmaplot and Excel statistical software.

Figure 1B:
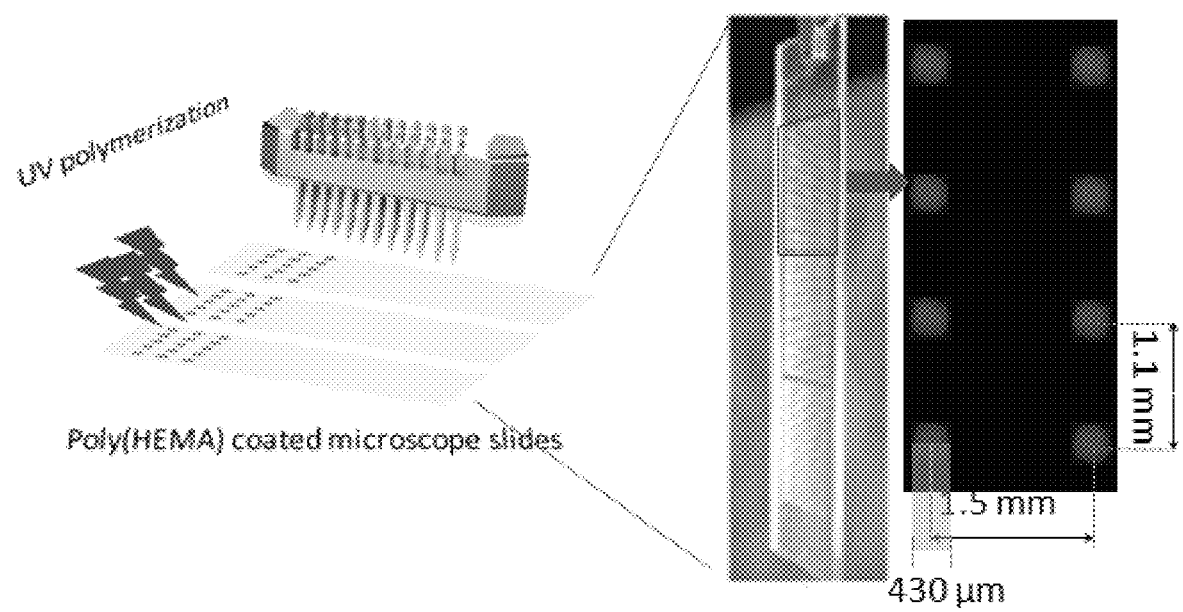
Figure 1C:
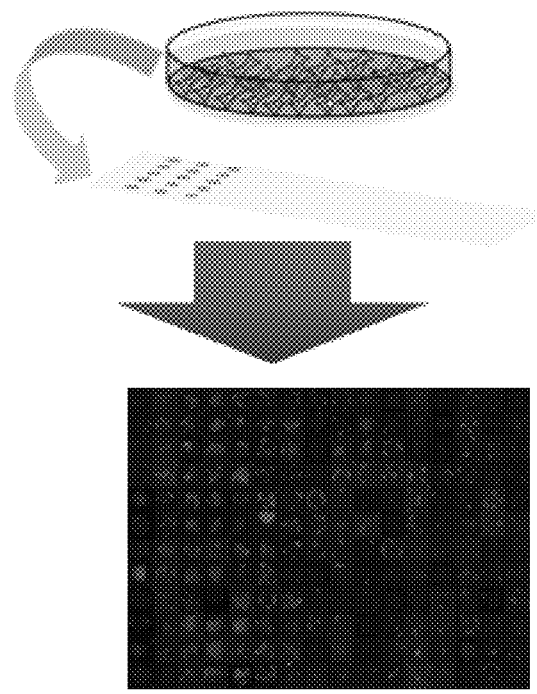

FIG. 1 shows a general strategy for the fabrication of peptide-functionalized PEG microarrays for stem cell and tissue engineering applications. To fabricate the microarrays, nanoliters of PEGDA and methacrylated-peptides have been robotically deposited onto poly(HEMA) coated glass slides and photo-polymerized in situ. This approach is chosen due to the high polymerization rate of photopolymerization and the high solubility of methacrylated-peptides in DMF. In addition, peptide-functionalized PEG hydrogels have been extensively employed in stem cell and tissue engineering applications. This makes it possible to quickly translate the screening results into design principles for the improved fabrication of 2D culture substrates and 3D scaffolds.

Figure 2:
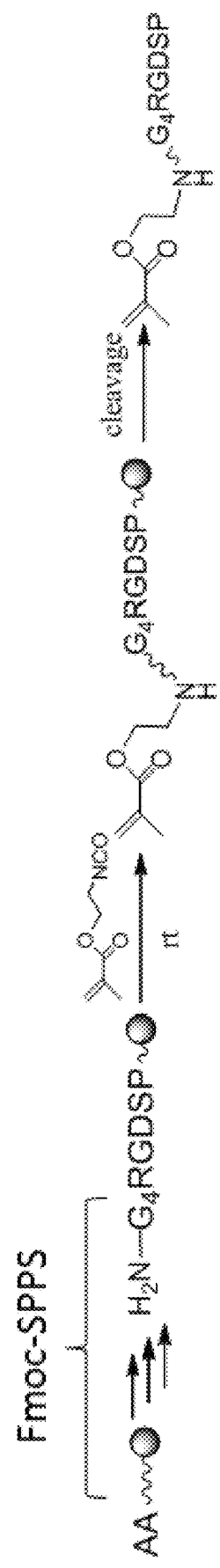
FIG. 2. The methacrylated peptides are prepared by conjugating 2-isocyanatoethyl methacrylate with the terminal amine of the peptides on the solid-phase.

FIG. 2 demonstrates a general procedure to prepare methacrylated-peptides. After solid-phase peptide synthesis, 2-isocyanatoethyl methacrylate was used to react with the terminal amine of the peptides in order to conjugate methacrylate groups. As the conjugation reaction step was right after peptide synthesis on the solid-phase, this route allows for the preparation of methacrylated-peptides from virtually any peptides. Further, this solid-phase conjugation reaction has been proven very effective and efficient.

To provide a low cell adhesion background for peptide screening, PEGDA of different molecular weights were screened to generate the non-fouling PEG hydrogel substrates. To this end, three commercially available low molecular weight PEGDA: PEGDA-250 (molecular weight, M. W.=250), PEGDA-575 (M. W.=575), PEGDA-700 (M. W.=700), have been used to fabricate an 8×8 microarray to screen for formulations that can resist non-specific cell adhesion. After seeding human adipose-derived stem cells (hADSCs) onto the hydrogel microarray, every spot composed of PEGDA-250 showed extensive cell adhesion. While the spots made by PEGDA-575 were right at the threshold to resist cell attachment (only 1 or 2 cells/spot), no cell attachment was recorded for those made of PEGDA-700 (FIG. 3). The differences in cell adhesion can be attributed to the ethylene glycol chain length of the PEGDA, as the longer ethyl glycol chain provides significantly enhanced chain flexibility to resist protein adsorption and cell adhesion. Since the spots prepared from the PEGDA-700 showed high resistance to non-specific cell adhesion, PEGDA-700 was selected to co-polymerize with methacrylated-peptides to prepare peptide-functionalized PEG hydrogel microarrays.

Figure 4:
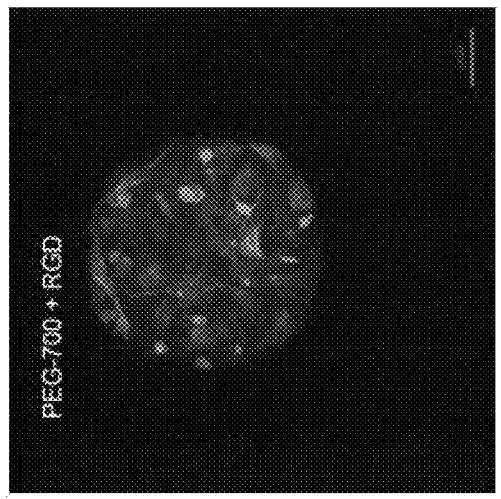
FIG. 4. Functional validation of the peptide moieties on the hydrogels. The representative fluorescent images of blank PEGDA-700 hydrogels (left), RDGSP (SEQ ID NO:34) functionalized PEGDA-700 hydrogels (middle) and RGDSP (SEQ ID NO:33) functionalized PEGDA-700 hydrogels (right) after hADSC seeding (blue: DAPI, green: phalloidin, scale bar=100 μm).
Figure 4:
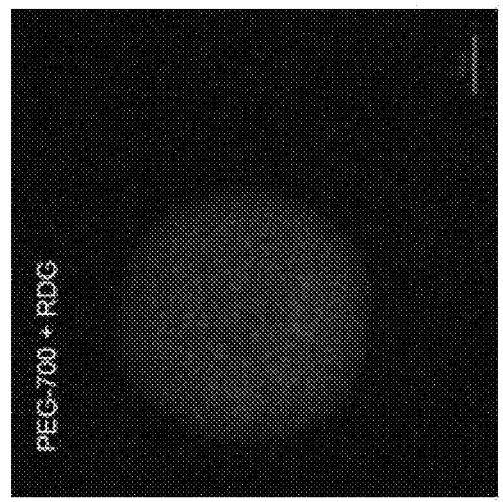
Figure 4:
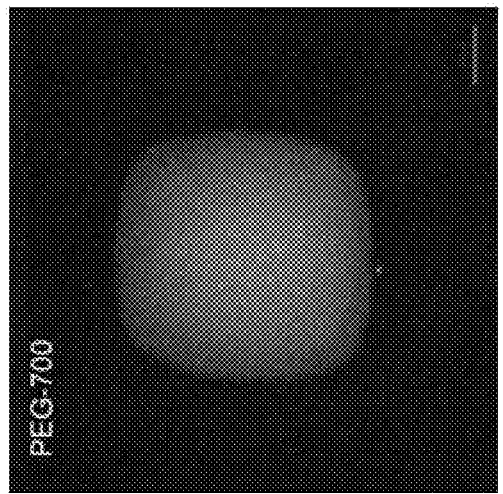

To validate the functions of the peptide moieties on the hydrogels, we synthesized a methacrylated-peptide containing a cell adhesive moiety (G$_4$RGDSP) (SEQ ID NO:46) and its scrambled sequence (G$_4$RDGSP) (SEQ ID NO:47). The methacrylated-peptides were then co-polymerized with PEGDA-700 to prepare PEG hydrogel spots functionalized with cell adhesive RGD (SEQ ID NO:36) peptides or the scrambled RDG (SEQ ID NO:36) peptide. As shown in the FIG. 4, PEG hydrogels modified with a high concentration of (15 mM) RGD-peptide were able to effectively promote adhesion of hADSCs (FIG. 4, right), while no cell adhesion was found on the scrambled peptide DG (SEQ ID NO:36) functionalized PEG hydrogels (FIG. 4, middle). These results indicate the function of peptides is retained during the microarray fabrication process.

Figure 5C:
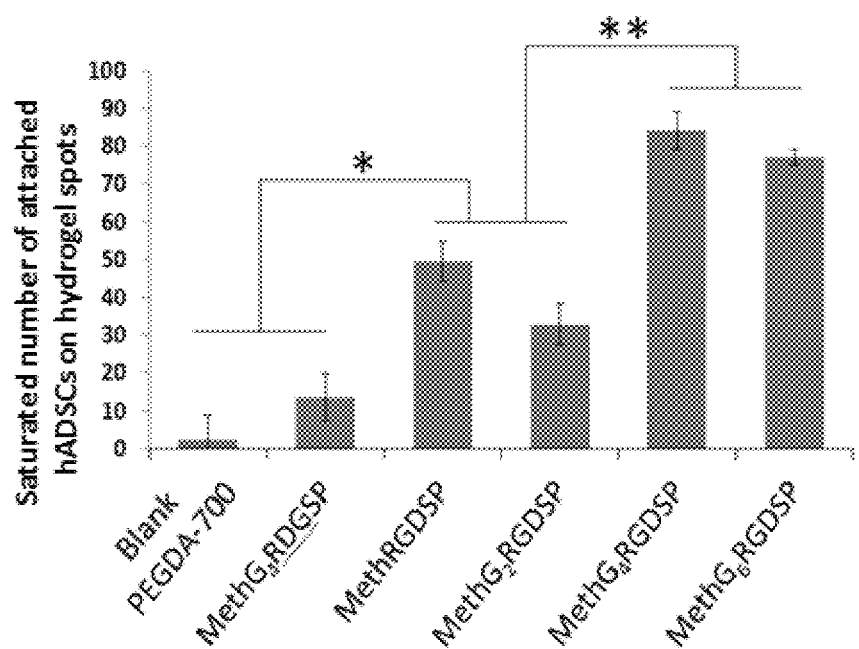

The length of the linker between peptide moiety and hydrogel surface has been shown to significantly influence peptide activities and further affect cell behavior. While there is one ethylene glycol group between methacrylate and the cell-binding peptide moiety, it may not be sufficient to ensure the exposure of the peptides on the hydrogel surface for cell recognition. Enlightened by the idea of using a 4-glycine linker to extend the RGD (SEQ ID NO:36) peptide from hydrogel surface, we designed and synthesized methacrylated-RGDSP-peptides with no glycine linker (MethRGDSP) (SEQ ID NO:33), 2 glycine linker (MethG$_2$RGDSP) (SEQ ID NO:45), 4 glycine linker (MethG$_4$RGDSP) (SEQ ID NO:46) and 6 glycine linker (MethG$_6$RGDSP) (SEQ ID NO:48), as listed in FIG. 5A. The microarrays composed with these peptides have been fabricated and hADSCs were seeded onto the array. Sigmoidal relationships between the number of attached cells and peptide concentration were found for all of these RGD (SEQ ID NO:36) peptides (FIG. 5B). Given the sigmoidal relationship, small changes in peptide concentration can result in large shifts in cell attachment numbers at lower peptide concentrations. To reduce variation in the high throughput analysis, the saturated (maximum) number of attached cells has been used to examine the effects of changing glycine linker length (FIG. 5C). MethG$_4$RGDSP (SEQ ID NO:46) and MethG$_6$RGDSP (SEQ ID NO:48) showed similar saturation numbers for attached cells (FIGS. 5B and 5C). They are about one-fold higher than the saturation number of attached cells of MethRGDSP (SEQ ID NO:33) and MethG$_2$RGDSP (SEQ ID NO:45). These results indicate that longer linkers improved the exposure of the peptides on the hydrogel surface. Also, the similar cell attachment between MethG$_4$RGDSP (SEQ ID NO:46) and MethG$_6$RGDSP (SEQ ID NO:48) suggested that 4 glycine provides sufficient length as a linker between the methacrylate and peptide components for our system. Therefore, further experiments were performed using peptides modified with the four-glycine linker.

The newly developed peptide-functionalized hydrogel microarray will allow us to rapidly identify novel peptides to functionalize biomaterials for numerous stem cell and tissue engineering applications. To this end, we used this technology to screen adhesion peptides for human induced pluripotent stem cell-derived cardiomyocytes (hiPSC-CMs). While hiPSC-CMs hold remarkable promise as a cell source to treat cardiovascular diseases, they have been reported as having poor adhesion on synthetic substrates. hiPSC-CMs express integrin $\alpha_3$, $\alpha_5$, $\alpha_6$, $\alpha_7$, $\alpha_v$, $\beta_1$ and $\beta_5$. Given the high affinity of RGD (SEQ ID NO:36) peptides to integrin $\alpha_v\beta_5$, we reasoned that RGD (SEQ ID NO:36) peptide functionalization can improve the binding affinity of PEG hydrogel substrates to hiPSC-CMs. To rapidly identify RGD (SEQ ID NO:36) peptide candidates with the potential of high affinity to hiPSC-CMs, we utilized an online bioinformatics tool (UniProtKB database) to screen and align the whole sequence of fibronectin, vitronectin and laminin through multiple species. We selected 12 different RGD (SEQ ID NO:36) peptides (FIG. 6B) to construct a PEG hydrogel microarray functionalized with these peptides. The candidates include: 1) 6 RGD (SEQ ID NO:36) peptides that have been reported to improve cell adhesion, such as those selected from laminin-$\alpha$1, laminin-$\alpha$5, fibronectin and vitronectin, and 2) 6 RGD (SEQ ID NO:36) peptides that have not been studied, but have been shown to be highly conserved sequences among the different mammalian species. The highly conserved RGD (SEQ ID NO:36) sequences among different mammalian species indicate their importance for certain fundamental functions (e.g. cell adhesion/ integrin binding). One RGD (SEQ ID NO:36) peptide (PQVTRGDVFTMP, SEQ ID NO:37) from vitronectin, has been included in the microarrays as a control as they were shown to support adhesion of hiPSC-CMs.

hiPSC-CMs were seeded onto the RGD (SEQ ID NO:36) peptides functionalized PEG hydrogel microarrays to examine the abilities of different RGD (SEQ ID NO:36) peptides for the enhanced cell adhesion. The cell adhesion response varied among the hydrogels: ~50% of RGD (SEQ ID NO:36) peptides could not support adhesion of hiPSC-CMs (FIGS. 6A-a, 6A-b), some RGD (SEQ ID NO:36) peptides (e.g., PQVTRGDVFTMP, SEQ ID NO:37 and SETQRGDVFVP, SEQ ID NO:30) support moderate cell adhesion (FIG. 6A-c), and PMQKMRGDVFSP (SEQ ID NO:6) (laminin 34 chain) showed the greatest ability to promote hiPSC-CM adhesion and sarcomere formation, a critical step for cardiomyocytes maturation (FIGS. 6A-d). The screening results have been validated with 18 replicates. It is worthwhile to note 2 out of 6 unexplored RGD (SEQ ID NO:36) peptides (PMQKMRGDVFSP, SEQ ID NO:6, DAVKQLQAAERGDA, SEQ ID NO:5) have shown substantial activities to support hiPSC-CM adhesion. This supports our hypothesis that highly conserved RGD (SEQ ID NO:36) peptide sequences among different species indicate their importance in functions (e.g., cell adhesion/integrin binding). This highlights the power of the combination of the microarray technology we developed here and the bioinformatics tool we utilized to rapidly identify novel biological ligands for the development of functional biomaterials for stem cell and tissue engineering applications. To the best of our knowledge, the highest cell adhesive peptide identified in this study, PMQKMRGDVFSP (SEQ ID NO:6) from laminin β4 subunit, has not been recognized as being a cell-adhesive peptide. Our current research includes the utilization of this novel RGD (SEQ ID NO:36) peptide from laminin β4 subunit to prepare 3D scaffolds for cardiac tissue engineering applications. Notably, the RGD (SEQ ID NO:36) peptide from vitronectin (PQVTRGDVFTMP, SEQ ID NO:37) showed moderate binding affinity for hiPSC-CMs (FIG. 6C), which could explain a previous report that hiPSC-CMs detach from synthetic substrates during the cardiac differentiation process.

We also examined the effects of the peptide sequences on sarcomere formation of hiPSC-CMs using sarcomeric actinin staining (FIGS. 6A, E), as sarcomeres are structural and functional units for cardiomyocytes contractions. The trend of alpha sarcomeric actinin expression per cell was found similar to that of cell adhesion (i.e., the affinities of peptide ligands). This can be attributed to that the high affinity peptide ligands can provide sufficient support for cardiomyocyte contractions and facilitate sarcomere formation. Consistent with the cell adhesion results, the RGD (SEQ ID NO:36) peptide from laminin β4 subunit supported hiPSC-CMs with the highest sarcomeric actinin expression. With the assistance from confocal microscope, the detailed sarcomere structures were revealed. This data suggests the RGD (SEQ ID NO:36) peptide from laminin 14 subunit can effectively support hiPSC-CM attachment, spreading and contractile structure development. These results are in agreement with a recent report that showed integrin binding is essential for hiPSC-CM maturation.

Recent advances in stem cell and tissue engineering strategies highlight an unmet need to rapidly identify suitable biomaterials for cell-specific applications. Here we developed a peptide-functionalized PEG hydrogel microarray based on light-assisted, co-polymerizations between poly(ethylene glycol) diacrylates (PEGDA) and methacrylated-peptides. By leveraging solid-phase peptide/organic synthesis, methacrylate-peptides can be synthesized from virtually any peptide sequences. When combined with a cell-adhesion resistant hydrogel derived from PEGDA-700, we have developed a framework for fabricating peptide-functionalized hydrogel microarrays. In addition, we identified a linker composed of 4 glycines that can ensure sufficient exposure for the peptide moieties on the hydrogel surface. Lastly, we combined peptide-functionalized microarray technology with bioinformatics to identify novel biological ligands with high affinity to hiPSC-CMs, a cell type known for poor adhesion to synthetic substrates. Among 6 unexplored RGD (SEQ ID NO:36) peptides, 2 peptides showed substantial affinity to hiPSC-CMs. PMQKMRGDVFSP (SEQ ID NO:6) from laminin 14 subunit, a peptide that had not previously been recognized as being cell adhesive, was found to have the highest affinity to hiPSC-CMs and the most developed sarcomere structures.

The technology we developed here can allow for the rapid identification of biological ligands for stem cell and tissue engineering application. As peptide-functionalized PEG hydrogels are widely used in stem cell and tissue engineering applications, the screening results could be quickly translated to 2D substrates and 3D scaffold fabrication. Although PEGDA-700 was used to fabricate hydrogel to resist non-specific cell adhesion in this study, clearly, PEGDA-700 can be replaced with another non-fouling hydrogel-precursors (e.g., PEGDA 3400, methacrylated hyaluronic acids) to vary the bulk properties (e.g., stiffness) of the hydrogel substrates. Our next step is to fabricate hydrogel microarrays that can cover the entire physiological/pathological range of stiffnesses. The ability to rapidly screen the combined effects of biological ligands and mechanical properties on (stem) cells can dramatically accelerate the advancement of the fundamental understanding of the interaction (stem) cell activity and biomaterials. This would further contribute to the development of biomaterial genomics through Big Data analytics.

Finally, the peptide-functionalized hydrogel microarrays developed here can find many applications in biomedical-related fields beyond stem cell and tissue engineering. We can envision that peptide-functionalized hydrogel microarrays will be used to develop anti-infectious substrates, given the wide application of the peptides and hydrogels for designing anti-infectious materials. Thus, the present invention provides products and methods of treating infections caused by bacteria, fungi, viruses, and parasites.

Bacterial infections that can be affected using the present invention can be caused by bacteria such as gram-negative bacteria. Examples of gram-negative bacteria include, but are not limited to, bacteria of the genera *Salmonella, Escherichia, Klebsiella, Haemophilus, Pseudomonas, Proteus, Neisseria, Vibro, Helicobacter, Brucella, Bordetella, Legionella, Campylobacter, Francisella, Pasteurella, Yersinia, Bartonella, Bacteroides, Streptobacillus, Spirillum* and *Shigella*. Furthermore, bacterial infections that can be treated using the sanitizing compositions of the present invention can be caused by gram-negative bacteria including, but not limited to, *Escherichia coli, Pseudomonas aeruginosa, Neisseria meningitides, Neisseria gonorrhoeae, Salmonella typhimurium, Salmonella entertidis, Klebsiella pneumoniae, Haemophilus influenzae, Haemophilus ducreyi, Proteus mirabilis, Vibro cholera, Helicobacter pylori, Brucella abortis, Brucella melitensis, Brucella suis, Bordetella pertussis, Bordetella parapertussis, Legionella pneumophila, Campylobacter fetus, Campylobacter jejuni, Francisella tularensis, Pasteurella multocida, Yersinia pestis, Bartonella bacilliformis, Bacteroides fragilis, Bartonella henselae, Streptobacillus moniliformis, Spirillum minus* and *Shigella dysenteriae*.

Bacterial infections that can be affected using the present invention can also be caused by bacteria such as gram-positive bacteria. Examples of gram-positive bacteria include, but are not limited to, bacteria of the genera *Listeria, Staphylococcus, Streptococcus, Bacillus, Corynebacterium, Peptostreptococcus,* and *Clostridium*. Furthermore, bacterial infections that can be treated using the sanitizing compositions of the present invention can be caused by gram-positive bacteria including, but not limited to, *Listeria monocytogenes, Staphylococcus aureus, Streptococcus pyogenes, Streptococcus pneumoniae, Bacillus cereus, Bacillus anthracis, Clostridium botulinum, Clostridium perfringens, Clostridium difficile, Clostridium tetani, Corynebacterium diphtheriae* and *Peptostreptococcus anaerobius*. In some embodiments, the gram-positive bacterium is methicillin-resistant *Staphylococcus aureus*.

Additional bacterial infections that can be affected using the present invention can be caused by bacteria in the genera including, but not limited to, *Actinomyces, Propionibacterium, Nocardia* and *Streptomyces*. Furthermore, bacterial infections that can be treated using the sanitizing compositions of the present invention can be caused by bacteria including, but not limited to, *Actinomyces israeli, Actinomyces gerencseriae, Actinomyces viscosus, Actinomyces naeslundii, Propionibacterium propionicus, Nocardia asteroides, Nocardia brasiliensis, Nocardia otitidiscaviarum* and *Streptomyces somaliensis*.

The effect on bacterial infections described herein can be bacteriocidal or bacteriostatic.

Mycobacterial infections that can be affected by the present invention can be caused by mycobacteria belonging to the mycobacteria families including, but not limited to, Mycobacteriaceae. Additionally, mycobacterial infections that can be treated by the sanitizing compositions of the present invention can be caused by mycobacteria including, but not limited to, *Mycobacterium tuberculosis, Mycobacterium leprae, Mycobacterium avium-intracellulare, Mycobacterium kansasii,* and *Mycobacterium ulcerans*.

Fungal infections that can be affected by the present invention can be caused by fungi belonging to the genera including, but not limited to, *Aspergillus, Candida, Cryptococcus, Coccidioides, Tinea, Sporothrix, Blastomyces, Histoplasma,* and *Pneumocystis*. Additionally, fungal infections that can be treated using the sanitizing compositions of the present invention can be caused by fungi including, but not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum,* and *Histoplasma duboisii.*

Viral infections that can be treated using the sanitizing compositions of the present invention can be caused by viruses belonging to the viral families including, but not limited to, Flaviviridae, Arenaviradae, Bunyaviridae, Filoviridae, Poxviridae, Togaviridae, Paramyxoviridae, Herpesviridae, Picornaviridae, Caliciviridae, Reoviridae, Rhabdoviridae, Papovaviridae, Parvoviridae, Adenoviridae, Hepadnaviridae, Coronaviridae, Retroviridae, and Orthomyxoviridae. Furthermore, viral infections that can be treated using the sanitizing compositions of the present invention can be caused by the viruses including, but not limited to, Yellow fever virus, St. Louis encephalitis virus, Dengue virus, Hepatitis G virus, Hepatitis C virus, Bovine diarrhea virus, West Nile virus, Japanese B encephalitis virus, Murray Valley encephalitis virus, Central European tick-borne encephalitis virus, Far eastern tick-born encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Lymphocytic choriomeningitis virus, Junin virus, Bolivian hemorrhagic fever virus, Lassa fever virus, California encephalitis virus, Hantaan virus, Nairobi sheep disease virus, Bunyamwera virus, Sandfly fever virus, Rift valley fever virus, Crimean-Congo hemorrhagic fever virus, Marburg virus, Ebola virus, Variola virus, Monkeypox virus, Vaccinia virus, Cowpox virus, Orf virus, Pseudocowpox virus, Molluscum contagiosum virus, Yaba monkey tumor virus, Tanapox virus, Raccoonpox virus, Camelpox virus, Mousepox virus, Tanterapox virus, Volepox virus, Buffalopox virus, Rabbitpox virus, Uasin gishu disease virus, Sealpox virus, Bovine papular stomatitis virus, Camel contagious ecthyma virus, Chamios contagious ecthyma virus, Red squirrel parapox virus, Juncopox virus, Pigeonpox virus, Psittacinepox virus, Quailpox virus, Sparrowpox virus, Starlingpox virus, Peacockpox virus, Penguinpox virus, Mynahpox virus, Sheeppox virus, Goatpox virus, Lumpy skin disease virus, Myxoma virus, Hare fibroma virus, Fibroma virus, Squirrel fibroma virus, Malignant rabbit fibroma virus, Swinepox virus, Yaba-like disease virus, Albatrosspox virus, Cotia virus, Embu virus, Marmosetpox virus, Marsupialpox virus, Mule deer poxvirus virus, Volepox virus, Skunkpox virus, Rubella virus, Eastern equine encephalitis virus, Western equine encephalitis virus, Venezuelan equine encephalitis virus, Sindbis virus, Semliki Forest virus, Chikungunya virus, O'nyong-nyong virus, Ross River virus, parainfluenza virus, mumps virus, measles virus (rubeola virus), respiratory syncytial virus, Herpes simplex virus type 1, Herpes simplex virus type 2, Varicella zoster virus, Epstein-Barr virus, Cytomegalovirus, human b-lymphotrophic virus, human herpesvirus 7, human herpesvirus 8, poliovirus, Coxsackie A virus, Coxsackie B virus, ECHOvirus, rhinovirus, Hepatitis A virus, mengovirus, ME virus, encephalomyocarditis (EMC) virus, MM virus, Columbia SK virus, Norwalk agent, Hepatitis E virus, Colorado tick fever virus, rotavirus, vesicular stomatitis virus, rabies virus, papilloma virus, BK virus, JC virus, B19 virus, adeno-associated virus, adenovirus (including serotypes 3, 7, 14, 21), Hepatitis B virus, coronavirus, human T-cell lymphotrophic virus, human immunodeficiency virus, human foamy virus, influenza viruses, types A, B, C, and thogotovirus.

Parasitic infections that can be affected by the present invention can be caused by parasites belonging to the genera including, but not limited to, *Entamoeba, Dientamoeba, Giardia, Balantidiuwn, Trichomonas, Cryptosporidium, Isospora, Plasmodium, Leishmania, Trypanosoma, Babesia, Naegleria, Acanthamoeba, Balamuthia, Enterobius, Strongyloides, Ascaradia, Trichuris, Necator, Ancylostoma, Uncinaria, Onchocerca, Mesocestoides, Echinococcus, Taenia, Diphylobothrium, Hymenolepsis, Moniezia, Dicytocaulus, Dirofilaria, Wuchereria, Brugia, Toxocara, Rhabditida, Spirurida, Dicrocoelium, Clonorchis, Echinostoma, Fasciola, Fascioloides, Opisthorchis, Paragonimus,* and *Schistosoma.* Additionally, parasitic infections that can be treated using the sanitizing compositions of the present invention can be caused by parasites including, but not limited to, *Entamoeba histolytica, Dientamoeba fragilis, Giardia lamblia, Balantidium coli, Trichomonas vaginalis, Cryptosporidium parvum, Isospora belli, Plasmodium malariae, Plasmodium ovale,* 20 *Plasmodium falciparum, Plasmodium vivax, Leishmania braziliensis, Leishmania donovani, Leishmania tropica, Trypanosoma cruzi, Trypanosoma brucei, Babesia divergens, Babesia microti, Naegleria fowleri, Acanthamoeba culbertsoni, Acanthamoeba polyphaga, Acanthamoeba castellanii, Acanthamoeba astronyxis, Acanthamoeba hatchetti, Acanthamoeba rhysodes, Balamuthia mandrillaris, Enterobius vermicularis, Strongyloides stercoralis, Strongyloides filleborni, Ascaris lumbricoides, Trichuris trichiura, Necator americanus, Ancylostoma duodenale, Ancylostoma ceylanicum, Ancylostoma braziliense, Ancylostoma caninum, Uncinaria stenocephala, Onchocerca volvulus, Mesocestoides variabilis, Echinococcus granulosus, Taenia solium, Diphylobothrium latum, Hymenolepis ana, Hymenolepis diminuta, Moniezia expansa, Moniezia benedeni, Dicytocaulus viviparous, Dicytocaulus filarial, Dicytocaulus arnfieldi, Dirofilaria repens, Dirofilaria immitis, Wuchereria bancrofti, Brugia malayi, Toxocara canis, Toxocara cati, Dicrocoelium dendriticum, Clonorchis sinensis, Echinostoma, Echinostoma ilocanum, Echinostoma jassyenese, Echinostoma malayanum, Echinostoma caproni, Fasciola hepatica, Fasciola gigantica, Fascioloides magna, Opisthorchis viverrini, Opisthorchis felineus, Opisthorchis sinensis, Paragonimus westermani, Schistosoma japonicum, Schistosoma mansoni, Schistosoma haematobium* and *Schistosoma haematobium.*

Example 2: Polymer Microarray Technology Enabled Discovery of a Bi-Functional RGD Peptide that Promotes Endothelial Cell Adhesion, Spreading and Proliferation We used the peptide-functionalized hydrogel microarray technology described in the Example 1 to screen the RGD (SEQ ID NO:36) peptide library for the high affinity ligands to endothelial cell (EC) integrin. This enabled the identification of a novel RGD (SEQ ID NO:36) peptide ($\alpha$1) derived from laminin-$\alpha$1 domain with dramatically enhanced ability to promote EC adhesion, spreading and proliferation in comparison with the currently used RGDS (SEQ ID NO:35)/RGDS (SEQ ID NO:35) peptide. The mechanistic studies revealed the $\alpha$1 peptide binds to both $\alpha$v$\beta$3 and VLA-6 integrin that lead to the synergistic up-regulation of VEGFR2 with the improved EC functions.

Materials and Instruments.

All chemicals used for this study were purchased from Sigma-Aldrich (St. Louis, Mo.) unless otherwise stated. Microarray spotting pins (946MP9B) were purchased from Arrayit Corporation (Sunnyvale, Calif.). A custom designed microarrayer was assembled by BioDot (Irvine, Calif.). The LC-MS system used is Thermo Fisher LCQ Fleettm Ion Trap Mass Spectrometer. Primary and secondary antibodies were purchased from Abcam (Cambridge, UK). The primers for RT-PCR were purchased from ThermoFisher Scientific Inc. (Waltham, Mass.). Sodium alginate was purchased from FMC BioPolymer (Philadelphia, Pa.).

Cell Culture.

Human umbilical vein endothelial cells (HUVECs) (Lonza, Basel, Switzerland) were cultured in EGMTM-2 BulletKit™ Medium (Lonza, Basel, Switzerland). The medium supplements contained 2% bovine serum albumin, hFBF-B, VEGF, R3-IGF-1, ascorbic acid, heparin, FBS, hEGF and GA-1000. Growth medium was changed every other day and cells were passaged every 6 days. All experiments were conducted using passage 4 (P4) HUVECs.

Synthesis and Characterization of N-Terminal Unmodified Peptides and Methacrylated Peptides.

Peptides used in this work were synthesized by solid phase peptide synthesis (SPPS). The SPPS was conducted using the standard procedure as described in Novabiochem peptide synthesis manual. N-terminal unmodified peptides were cleaved from resin right after the deprotection once reaching the designed sequences. To prepare methyacrylated peptides, 2-isocyanatoethyl methacrylate (3 equivalent (eq) dissolved in DMF) was used to react with the terminal amine group of the peptide chain (1 eq) before they were cleaved from the resin as described in the Example 1. All the peptides were purified by flash column and characterized by LC-MS.

Microarray Fabrication and Screening.

Methacrylated peptides (shown in FIG. 7) were dissolved in DMF at pre-designated ratios (1 mM, 3 mM, 6 mM, 9 mM, 12 mM, 15 mM and 20 mM) and mixed with PEGDA (containing 1% DMPA as initiator) (DMF solution of methacrylated peptide: PEGDA=1:1 (v/v)) and then transferred into a 384 well plate for microarray fabrication. The microarrays were printed in a humid Ar-atmosphere on epoxy monolayer-coated glass slides (Xenopore XENO-SLIDE E, Hawthorne, N.J.) which were first dip-coated in 4 v/v % poly(hydroxyethyl methacrylate) (i.e., poly(HEMA)) using a customized microarrayer (Biodot). Spots were polymerized via 10 s exposure to long wave UV (365 nm), dried at <50 mtorr for at least 7 days. Before use, the chips were sterilized by UV for 30 min for each side, and then washed with PBS twice for 15 min to remove residual monomer or solvent. HUVECs (human umbilical vein endothelial cells from Lonza, Basel, Switzerland) were seeded onto the array and cultured for 12 hours. They were then fixed and stained with DAPI for cell number counting and phalloidin for F-actin to estimate cell spreading for the lead peptide identification.

Alginate Synthesis and Oxidation.

Sodium alginate was prepared using the method established by Bouhadir et al. The final oxidation of the alginate was 5%.

Peptides Conjugation on Alginate Hydrogel.

The peptides were conjugated onto the oxidized alginate by the EDC-NHS chemistry as reported by Rowley: using aqueous carbodiimide reacted with peptides (RGDS (SEQ ID NO:35), RGDSP (SEQ ID NO:33) and α1-peptide) onto the oxidized alginate. In order to secure sufficient cell attachment, 10% (w/w) peptide modification was performed into the alginate hydrogel.

Alginate Surface Culture Experiments.

The Ca2+ containing substrates for alginate crosslinking was prepared according to the literature. 50 μl, 1% alginate modified with peptides (RGDS (SEQ ID NO:35), RGDSP (SEQ ID NO:33) and α1-peptide, respectively) aqueous solution was transferred into each well in 96 well plates (3 replicates for each peptide). The alginate was left gelling for 40 min. Then the well plates were transferred into incubator for 10 min to melt the Ca2+ containing substrates. After Ca2+ containing substrates get removed, HUVECs were seeded onto the hydrogel layers and cultured for 12 hours. Then they were fixed and stained with DAPI for cell number counting and phalloidin for F-actin to estimate cell spreading.

Antibody Blocking Experiments on Alginate Surface.

The integrin antibodies and their combinations (no antibody, anti VLA-6 only, anti-integrin αvβ3 only and anti VLA-6+ anti-integrin αvβ3,) were aliquot into predesigned ratio (final ratios in the mixture: 1:20 for anti VLA-6, 1:100 for anti-integrin αvβ3) with PBS, respectively. The HUVECs were incubated with these antibodies for 15 min, sedimented by low speed centrifugation, suspended in 100 μl of serum-free MEM plus 0.02% BSA and then added into the 1% alginate gel coated wells. The wells were transferred into incubator for 6 hours. After that, unattached cells were rinsed from the wells and the attached cells were then fixed and stained with DAPI for cell number counting and phalloidin for F-actin.

Alginate Gel Culture Experiments.

The Ca2+ containing substrates for alginate crosslinking was prepared as the previous literature mentioned. Alginate modified with these peptides (RGDS (SEQ ID NO:35), RGDSP (SEQ ID NO:33) and α1-peptide, respectively) was dissolved into HUVECs culturing media to prepare 1% alginate solution. The solution was mixed with HUVECs at the density of 10 million cells/ml. 250 id mixture of the alginate and HUVECs was transferred into each well in 96 well plates (3 replicates for each peptide). The alginate was left gelling for 40 min. Then the well plates were transferred into incubator for 10 min to melt the Ca2+ containing substrates. After Ca2+ containing substrates get removed, HUVEC culturing media was added into each well and continue culture for additional two days. Media were changed every day. The cells were then fixed and stained with DAPI for cell number counting and phalloidin for F-actin to estimate cell spreading at day 0 and day 2. The fluorescent pictures were taken by a Leica TCS SP5 AOBS confocal microscope system. The total tubule length and the proliferation rates were measured.

RT-PCR.

Before PCR experiments, HUVECs were seeded in three different peptides (RGDS (SEQ ID NO:35), RGDSP (SEQ ID NO:33) and α1-peptide, respectively) modified 1% alginate gel. The cells were cultured for 6 hrs and then harvest for RNA isolation. Total RNA was isolated according to the kit and protocol of an RNeasy Micro Kit (Qiagen, Vinlo, Netherlands) with the addition of the QIAShredder (Qiagen) during the homogenization step for HUVECs. For each group, around 0.1 million cells were used for RNA isolation. At least 25 ng of total RNA for each group was used for cDNA synthesis by the Bio-Rad (Hercules, USA) iScript cDNA synthesis kit. qRT-PCR was executed with "best coverage" validated Taqman primers (Life Technologies, Carlsbad, USA) in 10 μl reactions for the following genes:

KDR (VEGFR2), ACTB, GAPDH. qRT-PCR Data was normalized as the change in cycle threshold (dCt) from the geometric mean of ACTB and GAPDH expression. Expression was analyzed using mRNA expression=2^(−(dCt)) and then normalized to the gene expression from RGDS (SEQ ID NO:35) samples.

Statistical Analysis.

The results were shown in the mean+standard derivation (SD) and analyzed using Excel statistical software.

Figure 8A:
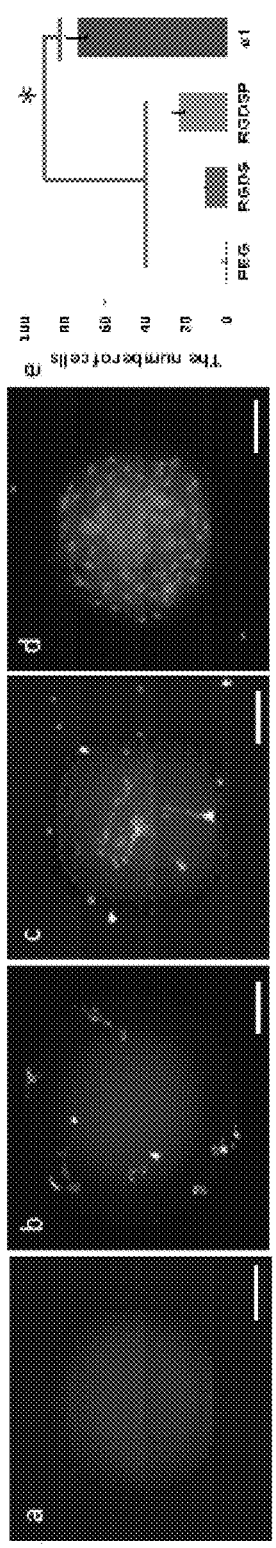
FIGS. 8A-F. Functional improvements of endothelial cells (EC) by α1 peptide and related mechanistic studies. (A) Adhesion of HUVECs to microarrayed PEG hydrogels functionalized with (a) no peptide (PEG), (b) RGDS (SEQ ID NO:35), (c) RGDSP (SEQ ID NO:33), (d) α1 peptide, and e: the related quantified cell adhesion. Blue-DAPI, Green-Phalloidin, scale bar is 100 um. (B) Adhesion of HUVECs to 2D alginates substrates hydrogels functionalized with 10% (w/w) peptide of a: RGDS (SEQ ID NO:35), b: RGDSP (SEQ ID NO:33), c: α1 peptide, and d: related quantified cell adhesion. Blue-DAPI, Green-Phalloidin, scale bar is 50 um. (C) HUVEC proliferation and network formation in 3D alginate hydrogels functionalized with 10% (w/w) peptide of (a) RGDS (SEQ ID NO:35), (b) RGDSP (SEQ ID NO:33), (c) α1 peptide, and (d) related quantified cell adhesion. Blue-DAPI, Green-Phalloidin, scale bar is 25 urn. (D) Adhesion of HUVECs treated with integrin blocking antibodies (x-axis) on 2D alginate substrates functionalized with RGDS (SEQ ID NO:35)/RGDSP (SEQ ID NO:34)/α1 peptide. (E) mRNA expression of VEGFR2 of HUVECs cultured in 3D alginate hydrogels functionalized with no peptide/RGDS (SEQ ID NO:35)/RGDSP (SEQ ID NO:34)/α1 peptide. (F) A schematic summary of the bi-functional α1 peptide capable of binding both $α_vβ_3$ and VLA-6 integrins and enhancing cell adhesion, proliferation and VEGFR2 expression.

To rapidly screen the peptide library for the high affinity RGD (SEQ ID NO:36) peptides to EC integrin, we fabricated microarrayed PEG (poly(ethylene glycol)) hydrogels that are functionalized with different RGD (SEQ ID NO:36) peptides as described the Example 1. We then seeded HUVECs (human umbilical vein endothelial cells) onto the microarrays. As shown in the FIG. 8A, a variety of different cell adhesions were found on the RGD (SEQ ID NO:36) peptide-functionalized PEG hydrogel microarray, which indicate different affinity of these RGD (SEQ ID NO:36) peptides to EC integrin. Hydrogel spots were used to quantify the peptide's affinity to EC integrin in this study.

RGD (SEQ ID NO:36) peptides derived from Fn, namely RGDS (SEQ ID NO:35) and RGDSP (SEQ ID NO:33), have been extensively used to promote EC adhesion, proliferation and network formation. Our data showed the RGDSP (SEQ ID NO:33) has significantly higher affinity to HUVECs than RGDS (SEQ ID NO:35) (FIG. 8A), which can be attributed to the additional proline at the chain end that reduces the flexibility of the RGDS (SEQ ID NO:35) peptide and increase its affinity towards integrin. These results are in agreement with the previous reports of the activities of these peptides to promote fibroblast attachment.

Among all the peptides in the library, a RGD (SEQ ID NO:36) peptide derived from Ln α1 subunit (α1 peptide, TFALRGDNP, SEQ ID NO:1) showed the highest activities to promote HUVEC adhesion (FIGS. 8A-D, E). The sequence of the α1 peptide was determined through the comparison of Laminin-α1 gene between human and chimpanzee, which demonstrates the powerful of the Bioinformatics tool we employed here. The saturated number of attached HUVECs of α1 peptide is ~200% higher than RGDSP (SEQ ID NO:33) and ~500% higher than RGDS (SEQ ID NO:35).

Figure 8B:
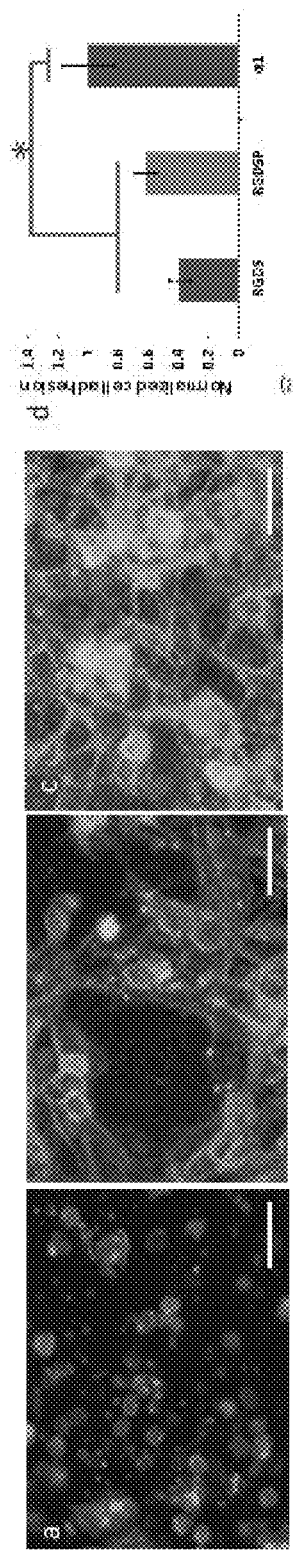
Figure 8C:
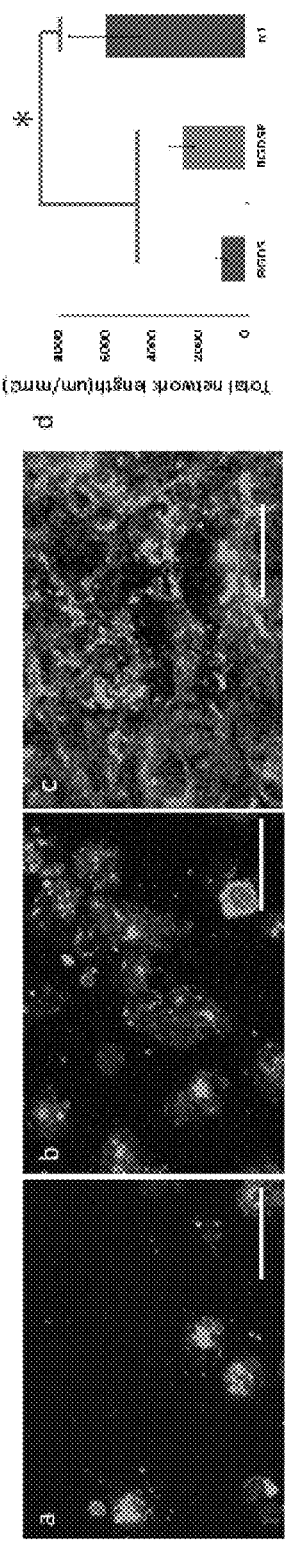
Figure 8D:
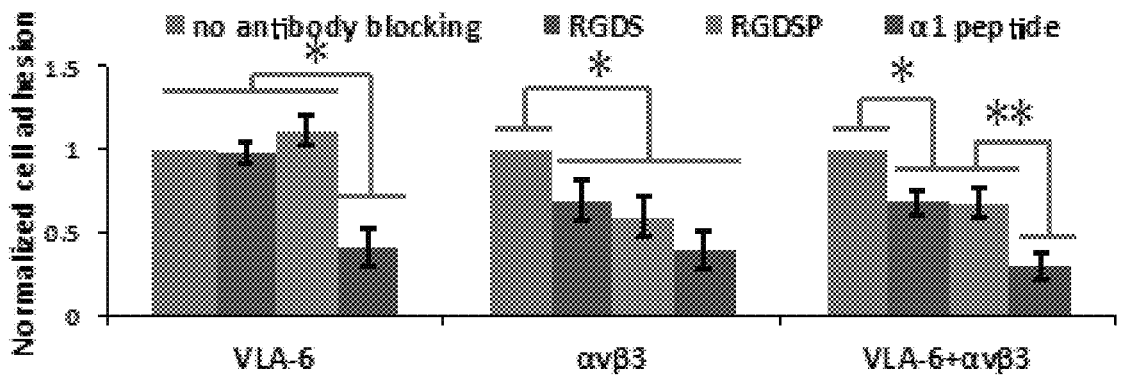

To prove the effectiveness of α1 peptide as a biological ligand, α1 peptide was conjugated onto alginate hydrogel. The number of HUVECs attached to 2D surface of α1 peptide-modified alginate hydrogel are ~60% higher than that of RGDSP (SEQ ID NO:33) and ~150% higher than that of RGDS (SEQ ID NO:35) (FIG. 8B). This data demonstrates the ability of α1 peptide to promote HUVEC adhesion and spreading on the surface of different hydrogel systems. As alginate has been widely used as a 3D cell culture system, we prepared RGDS (SEQ ID NO:35), RGDSP (SEQ ID NO:33) and α1 peptide functionalized 3D alginate hydrogels to examine their effects on HUVEC functions. Specifically, we used a 1% alginate with 10% (w/w) peptide functionalization to prepare 3D hydrogels contains 6 million HUVECs/ml. While F-actin staining of HUVECs in RGDS- and RGDSP-functionalized alginate hydrogels showed limited cell spreading and no visible network formation, the α1 peptide-functionalized alginate hydrogel showed significantly enhanced cell proliferation and network formation after 2 days culture (FIG. 8C). The extended culture of HUVECs in the hydrogels confirmed the enhanced proliferation of HUVECs in the α1 peptide functionalized alginate when compared with RGDS- and RGDSP-peptide functionalized alginates (FIG. 8C).

Figure 8E:
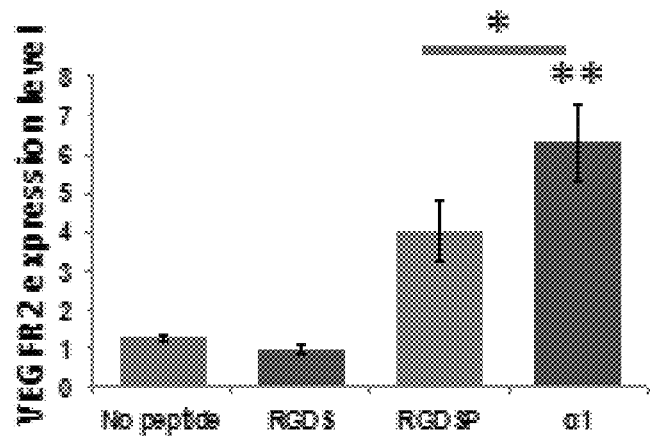
Figure 8F:
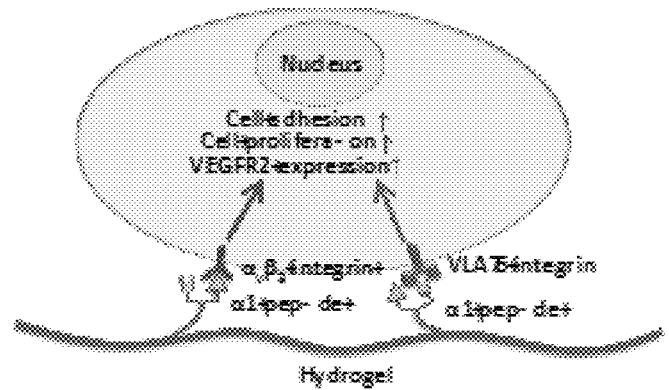

As described above, the α1 peptide was identified through the bioinformatics tool. To understand the mechanisms underpinning the enhanced adhesion, spreading and proliferation of HUVECs on/in the α1 peptide functionalized hydrogels, we conducted integrin-blocking experiments as a similar Ln derived peptide A99 (CQAGTFALRGDNPQG) (SEQ ID NO:49) was reported to bind to both VLA-6 (α6) and αvβ3 integrin subunits. As shown in the FIG. 8D, blocking VLA-6 integrin does not significantly affect cell adhesion for RGDS- and RGDSP-functionalized alginates, while it led to ~60% decrease in cell adhesion on the α1 peptide functionalized alginate. In addition, blocking αvβ3 integrin resulted in the ~35% decrease in cell adhesion for RGDS- and RGDSP-peptides functionalized alginates and ~60% decrease in cell adhesion for α1 peptide functionalized alginate. When both VLA-6 and αvβ3 integrin are blocked, ~35% decrease in the cell adhesion were found on the RGDS- and RGDSP-functionalized alginates and ~70% decrease in cell adhesion was found on α1 peptide functionalized alginate. These results clearly showed the RGDS- and RGDSP-peptides bind to αvβ3 integrin while the α1 peptide binds to both VLA-6 and αvβ3 integrin.

mRNA expression of VEGFR2 was significantly upregulated in the HUVECs cultivated in α1 peptide functionalized 3D alginate hydrogels when compared with RGDSP (SEQ ID NO:33) and RGDS (SEQ ID NO:35) samples after 6 hours culture (FIG. 8E). Interestingly, significant higher amount of VEGFR2 mRNA expression was found in HUVECs cultivated in RGDSP-peptide functionalized alginate hydrogels than those cultivated in RGDS-peptide functionalized alginate hydrogel, which was attributed to higher affinity of RGDSP (SEQ ID NO:33) peptide to αvβ3 integrin than RGDS (SEQ ID NO:35) peptide (FIGS. 8B and 8C).

To further confirm the co-signaling between αvβ3 and VLA-6 integrin binding, we prepared a co-signaling alginate hydrogel functionalized with both a αvβ3 binding peptide (RGDSP, SEQ ID NO:33) and a VLA-6 integrin binding peptide (LPSHYRARNI, SEQ ID NO:50). The synergy between RGDSP (SEQ ID NO:33) and LPSHYRARNI (SEQ ID NO:50) peptides led to significant improvement in VEGFR2 mRNA expression when compared with RGDSP-peptide functionalized alginate. Importantly, the combination of RGDSP (SEQ ID NO:33) and LPSHYRARNI (SEQ ID NO:50) peptides showed a similar capacity to improve HUVEC functions as the α1 peptide.

These results support our hypothesis that it is the ability of α1 peptide to engage both VLA-6 and αvβ3 integrin that leads to the synergistic up-regulation of VEGFR2 and results in enhanced HUVEC adhesion, spreading and proliferation. Co-signaling between integrin and growth factors has been utilized to develop functional hydrogels to improve EC vascularization and angiogenesis. To the best of our knowledge, this study, for the first time, demonstrates the co-signaling between two integrin binding ligands promotes EC adhesion, spreading and proliferation. We expect this co-signaling mechanism will allow for the development of next generation of biomaterials for the fabrication of vascularized tissue engineering constructs and 3D bioprinting applications. Further, integrin blocking has been used as a therapy for cancer treatments as integrin activation have been shown to play an essential role to promote angiogenesis in tumor growth. As the efficacy of the αvβ3 integrin binding peptides in suppressing pathological angiogenesis has been found to be rather moderate in clinical trials, the co-signaling mechanism identified here may provide an attractive means to develop next generation cancer therapeutics. Thus, the present invention provides products and methods of treating a tumor or cancer, wherein the tumor or cancer includes, prostate cancer, breast cancer, ovarian cancer, uterine cancer, pancreatic cancer, skin cancer, melanoma, lymphoma, sarcoma, lung cancer, colon cancer, leukemia, renal cancer, brain cancer, CNS cancer, neuroblastoma, oral cancer, throat cancer, esophageal cancer, head and neck cancer and combinations thereof.

In this study, we demonstrated the combination of modern bioinformatics and a newly established peptide-functionalized PEG hydrogel microarray technology enabled the identification of a novel RGD (SEQ ID NO:36) ($\alpha$1) peptide that promotes EC functions through co-activation of $\alpha v \beta 3$ and VLA-6 integrin. To the best of our knowledge, this is the first report that shows the synergy between $\alpha v \beta 3$ and VLA-6 integrin binding promotes VEGFR2 expression and EC adhesion, spreading and proliferation. The sequence of the $\alpha$1 peptide was defined through the comparison of Laminin-$\alpha$1 gene between human and chimpanzee, which demonstrates the power of the bioinformatics tool we used to identify potential candidates to construct peptide library. Further, the high affinity of $\alpha$1 peptide to HUVEC integrin was identified through the use of peptide-functionalized hydrogel microarrays and further validated by using 2D/3D hydrogels functionalized with the $\alpha$1 peptide. This demonstrates the effectiveness of the newly established peptide-functionalized hydrogel microarray to identify novel biological ligands to control (stem) cell behavior.

The moderate success of the tissue engineering approaches has been attributed to the insufficient vascularization within the scaffolds. Although numerous materials-based strategies have been explored to improve vascularization, few previous studies have been focused on the identification of novel biological ligands to improve the functions of ECs. While RGDS (SEQ ID NO:35)/RGDSP (SEQ ID NO:34) peptides have been routinely used to promote EC functions in vascularized tissue fabrication, our data demonstrates the dramatically improved performance of the $\alpha$1 peptide when compared with RGDS (SEQ ID NO:35)/RGDSP (SEQ ID NO:34) peptides. This highlights the power of the bioinformatics and the newly established peptide-functionalized hydrogel microarray technology in identifying novel biological ligands to regulate the functions of various (stem) cells.

Example 3: Synergistic Effect of Integrin-Binding Peptide and Angiogenic Factors We hypothesized that spatiotemporal distribution of VEGF mimetic QK peptide can significantly affect the crosstalk between $\alpha$1 peptide initiated integrin signaling and QK peptide initiated VEGFR2 signaling, which is important to EC morphogenesis and angiogenesis.

Figure 9:
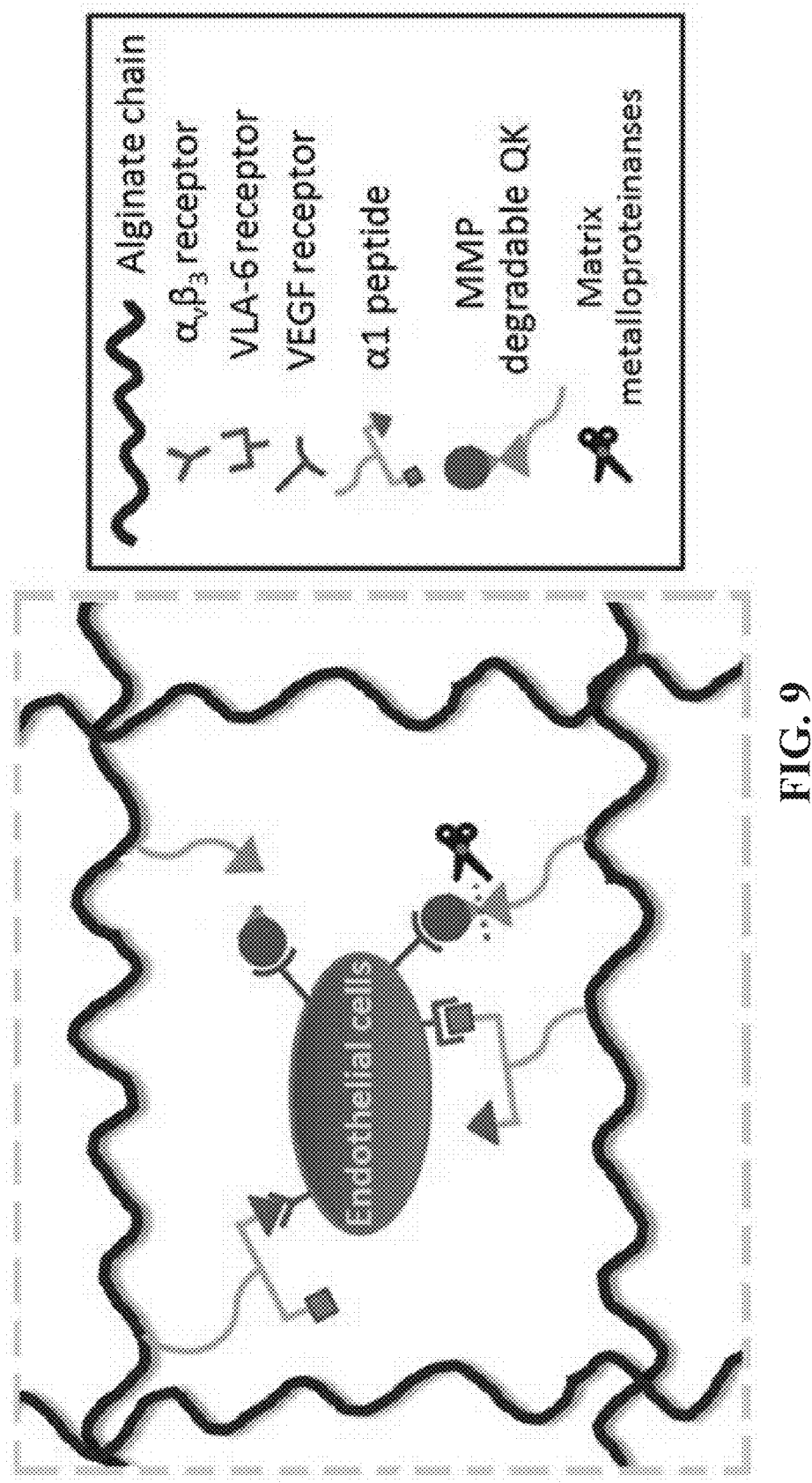
FIG. 9. Scheme of synergistic multi-signaling interactions between α1 peptide, QK peptide and EC surface receptors (i.e., $α_vβ_3$, VLA-6 integrins and VEGFR2).

To synergize with the $\alpha$1 peptide, we used the $\alpha$1 peptide and an MMP-responsive QK peptide (i.e., GPQ-G↓IAGKLTWQELYQLKYKGI, SEQ ID NO:41) to prepare an alginate-based injectable, multi-signaling hydrogels (FIG. 9). The MMP-responsive QK peptide was selected to introduce cell-dictated local release of angiogenic factors to recapitulate the pro-angiogenic microenvironment in vivo, where matrix bound VEGF is released by MMPs. Alginates was selected because it has been used as a biocompatible, injectable hydrogel-forming material to treat ischemic diseases.

Figure 10:
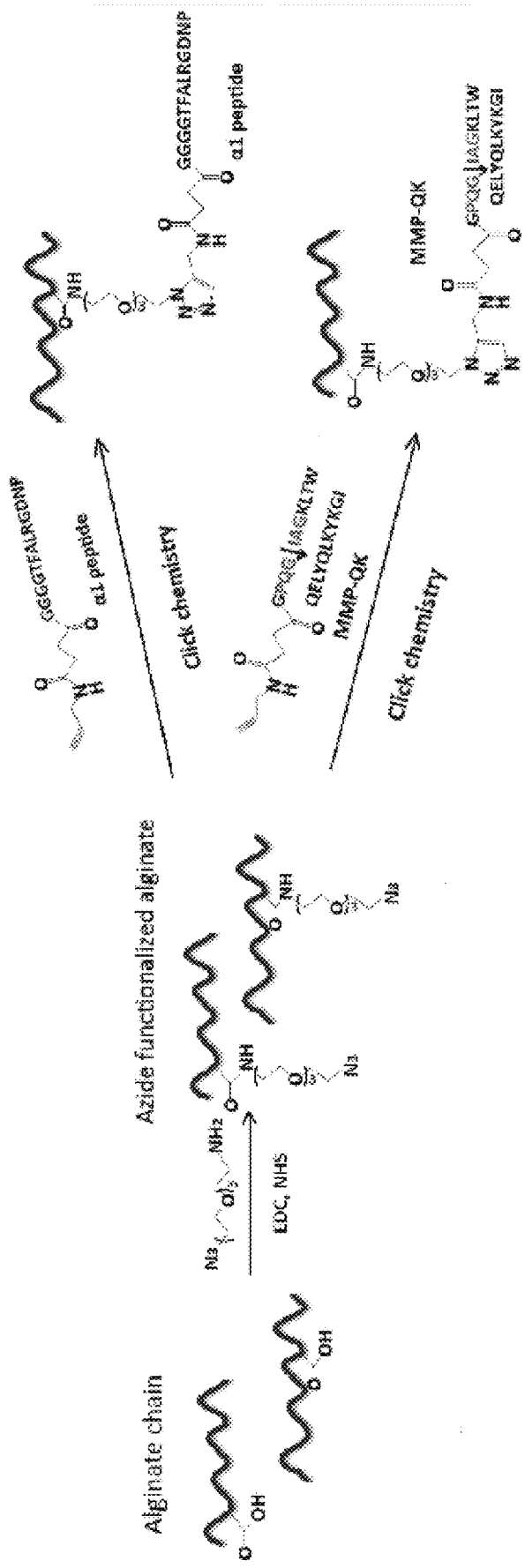
FIG. 10. Modular synthetic route to prepare α1 peptide functionalized alginates and MMP-responsive QK peptide (GPQG↓IAGKLTWQELYQLKYKGI, SEQ ID NO:41) functionalized alginates.

We developed a modular approach to prepare the multi-signaling hydrogels (FIG. 10). Briefly, we have prepared alginates functionalized with $\alpha$1 peptide (10% (w/w)) as well as alginates functionalized with MMP-responsive QK peptide (10% (w/w)) using click chemistry. We then mixed these two alginates at a ratio 1:1 (w/w) to prepare multi-signaling hydrogels to simultaneously engage $\alpha_v \beta_3$, VLA-6 integrins and VEGFR2. This modular approach allowed us to rapidly prepare alginates with different peptide functionalization to screen for an optimal formulation to support EC morphogenesis.

When compared with hydrogels functionalized with $\alpha$1 peptide and covalently bound QK and hydrogels functionalized with RGDSP (SEQ ID NO:33) peptide and MMP-responsive QK, the synergy between $\alpha$1 peptide and MMP-responsive QK peptide leads to the significant improvement in the EC vascular network formation (FIG. 11). These results clearly demonstrated the benefits of the combination of $\alpha$1 peptide and MMP-responsive QK peptide, which can collaboratively activate $\alpha_v \beta_3$ and VLA-6 integrins and controlled release VEGF mimetic peptide on cellular demand.

Our preliminary data clearly showed the synergy between $\alpha$1 peptide and MMP-responsive QK peptide leads to the significant improvement in the EC vascular network formation.

To prepare alginate hydrogel that can release QK peptide in a cellular demanded, temporally controlled manner, we will synthesize QK peptide with four different MMP sensitive linkers (QK (FL): QK with fast linker, QK (ML): QK with moderate linker, QK (SL): QK with slow linker, QK (NL): QK with non-degradable linker based on a recent report from Benoit and coworkers (Table 1). Notably, it was demonstrated that the activity of QK peptide is not affected by the presence of residue amino acids after MMP cleavage. These QK peptides will be conjugated to alginates using click chemistry as shown in the FIG. 10. In addition, we will mix alginates functionalized with QK (FL) and alginates functionalized with QK (SL) in a 50:50 (w/w) ratio to prepare the QK (PL) sample to create pulsatile release profile, which is a rapid release at the beginning followed by a sustained release at a lower rate. The pulsatile release profile was proposed as it was reported to optimally support EC sprouting.

TABLE 1

| MMP-responsive QK peptides with different protease sensitivity ||| 
|---|---|---|
| Abbreviation | Full | Sequences |
| QK (FL) | QK with fast linker | "QK"-PES↓LRAG (SEQ ID NO: 51) |
| QK (ML) | QK with moderate linker | "QK"-GPQG↓IWGQ (SEQ ID NO: 52) |
| QK (SL) | QK with slow linker | "QK"-VPLS""LYSG (SEQ ID NO: 53) |

TABLE 1-continued

MMP-responsive QK peptides with different protease sensitivity

| Abbreviation | Full | Sequences |
|---|---|---|
| QK (PL) | 50% QK with fast linker, 50% QK with slow linker | 50% "QK"-PES↓LRAG (SEQ ID NO: 51) and 50% "QK"-VPLS↓LYSG (SEQ ID NO: 53) |
| QK (NL) | QK with non-degradable linker | "QK"-GGGG (SEQ ID NO: 54) |

To examine the effects of the MMP-degradable linkage of the QK peptide on the EC morphogenesis, we will seed 6 million/ml HUVECs in 5% oxidized, 1% (w/w) alginates functionalized with 5% (w/w) α1 peptide and 5% (w/w) QK peptide with different MMP-degradable linkages (FL, ML, SL, PL, NL). After 2 days, the HUVECs will be fixed and stained with DAPI and phalloidin to quantify total network length per unit area. The vascular morphogenesis of the HUVECs will also further examined with immunofluorescence staining of CD31 and VE-Cadherin. This set of experiments will allow for the identification of optimal MMP-degradable linkage for the improved EC morphogenesis. Further, it would allow us to establish a relationship between the release profile of QK peptide and EC vascular network formation.

In addition to the temporal release profile, the concentrations of QK peptides can significantly affect EC functions. While our preliminary data demonstrated 5% (w/w) MMP-responsive QK peptides is sufficient to promote EC vascular network formation, additional experiments are necessary to identify the QK peptide concentration for the optimal EC morphogenesis. To this end, we will prepare alginate functionalized with different concentrations of the QK peptides with the optimized MMP-responsive linkage (i.e., 6%, 10%, 14%, 18% (w/w)) to examine their effects on EC functions. Briefly, we will vary the ratio between the 11-Azido-3,6,9-trioxaundecan-1-amine to alginate to prepare alginate with different azide-functionalization (—$N_3$), a linker for click chemistry conjugation (FIG. 10). These alginates will be reacted with alkyne-modified MMP-QK to prepare alginate functionalized with different concentrations of MMP-responsive QK peptides (i.e., 6%, 10%, 14%, 18% (w/w)). These alginates will be mixed with 10% (w/w) α1 peptide functionalized alginates at 1:1 (w/w) ration to prepare alginates functionalized with 5% (w/w) α1 peptide and different MMP-responsive QK concentration (i.e., 3%, 5%, 7% and 9% (w/w)). As described above, 6 million/ml HUVECs will be seeded into these alginates, cultured for 2 day and examined for the total network length. These experiments will allow for the identification of optimal concentration of MMP-responsive QK peptides for the in vive tests.

Example 4: In Vivo Pro-Angiogenic Potential of the Acelllar, Injectable Multi-Signaling Alginate Hydrogels We propose to inject alginate hydrogel functionalized with α1 peptide and optimized MMP-responsive QK peptide into the ischemic hindlimb of mouse to examine their pro-angiogenic potential. To prepare an injectable alginate hydrogel, 0.05 mM Ca gluconate solution will be mixed with 5% oxidized, 2% (w/w) alginate solution at the ratio 1:1 (v/v) to prepare the 1% injectable alginate hydrogels. High biocompatibility of this injectable hydrogel has been supported by the high viability of the HUVECs encapsulated in the gel (data not shown).

To induce unilateral hindlimb ischemia, a 10-week-old C57BL/6 mouse will be anesthetized and prepared for surgery. With a dissection microscope, we will dissect and separate the femoral artery from the femoral vein at the proximal location near the groin, pass a strand of 7-0 silk suture underneath the proximal end of the femoral artery and occlude the proximal femoral artery using double knots. Similarly, we will separate the femoral artery from the surrounding tissues at the distal location close to the knee, pass a strand of 7-0 suture underneath the distal end of the femoral artery proximal to the popliteal artery and occlude the vessel using double knots. We will then use spring scissors to transect the segment of femoral artery between the distal and proximal knots. 50 μL of 5% oxidized, 1% (w/w) alginate hydrogel functionalized with α1 peptide (5% w/w) and QK peptide with optimized MMP-degradable linkage and concentration will be injected into the quadricep (25 uL) and gastrocnemius (25 μL) muscles of the ischemic hind limb. Controls will include 50 μL of 5% oxidized, 1% (w/w) alginate functionalized with (1) no peptide, (2) 5% (w/w) α1 peptide (no QK), (3) the optimized QK peptide (no α1), (4) 5% (w/w) α1 peptide and QK peptide with a non-degradable linkage at the optimized concentration, (5) 5% (w/w) α1 peptide and QK peptide with an un-optimal MMP-degradable linkage at the optimized concentration, and (6) 5% (w/w) α1 peptide and QK peptide with an optimal MMP-degradable linkage at an un-optimized concentration, and (7) decellularized skeletal muscle extracellular matrix, a potential gold standard material to treat peripheral artery disease.

To examine the pro-angiogenic potential of the multi-signaling alginate hydrogel, the blood flow ratio between ischemic/normal limb will be measured before surgery as well as 1, 3, 5, 7, 14, 28 and 42 days post-surgery by using a Laser Doppler blood flow imaging system (Moor Instruments Ltd., Devon, UK). In addition, the hindlimb muscle tissues (n=7/condition, 42 days post-surgery) will be harvested, fixed, paraffin embedded and stained for CD31 (Abcam) to measure capillary densities. 30 randomly chosen fields of the tissue will be analyzed, and the total number of the blood vessels will be manually countered and normalized to the tissue area.

That which is claimed is:

1. A hydrogel composition comprising:
   (a) an integrin-binding peptide comprising the amino acid sequence TFALRGDNP (SEQ ID NO:1), TFALRADNP (SEQ ID NO:2), DVEKRGDREEAHVP (SEQ ID NO:3), IQRGDIDAMIS (SEQ ID NO:4), DAVKQLQAAERGDA (SEQ ID NO:5), PMQKMRGDVFSP (SEQ ID NO6), RSDGTG (SEQ ID NO:7), EAPRGDVYQG (SEQ ID NO:8), GLOGERGRO (SEQ ID NO:9), GFOGERGVQ (SEQ ID NO:10), DGEA (SEQ ID NO:11), GFOGER (SEQ ID NO:12), GLKGEN (SEQ ID NO:13), LDV (SEQ ID NO:14), REDV (SEQ ID NO:15), PEDGIHE (SEQ ID NO:16), PHSRN (SEQ ID NO:17), ALNGR (SEQ ID NO:18), IAFQRN (SEQ ID NO:19), IKLLI (SEQ ID NO:20), AGQWHRVSVRWG (SEQ ID NO:22), TWSQKALHHRVP (SEQ ID NO:23), SIYITRF (SEQ ID NO:24), SYWYRIEASRTG (SEQ ID NO:25), YIGSR (SEQ ID NO:26), RDIAEIIKDI (SEQ ID NO:27), VFDNFVLK (SEQ ID NO:28), AEIDGIEL (SEQ ID NO:29), SETQRGDVFVP (SEQ ID NO:30), PASYRGDSC (SEQ ID NO:31), VTGRGDSPAS (SEQ ID NO:32), PQVTRGDVFTMP (SEQ ID NO:37), or variants at least 90% identical thereto;
   (b) a pro-angiogenic growth factor and/or a VEGF mimetic peptide comprising the amino acid sequence KLTWQELYQLKYKGI (SEQ ID NO:38); and
   (c) a biocompatible polymer, wherein the integrin-binding peptide is linked to the biocompatible polymer.

2. The hydrogel composition of claim 1, wherein the linkage is a covalent or non-covalent linkage.

3. The hydrogel composition of claim 1, wherein the biocompatible polymer is functionalized with a VEGF or the VEGF mimetic peptide, which comprises the amino acid sequence KLTWQELYQLKYKGI (SEQ ID NO:38), and the integrin-binding peptide binds at least one type of endothelial cell integrin.

4. The hydrogel composition of claim 2, wherein the pro-angiogenic growth factor or the VEGF mimetic peptide is attached to the biocompatible polymer through a matrix metalloproteinase (MMP) degradable peptide linkage.

5. The hydrogel composition of claim 1, wherein the biocompatible polymer is functionalized with a VEGF or the VEGF mimetic peptide, which comprises the amino acid sequence KLTWQELYQLKYKGI (SEQ ID NO:38), and the integrin binding peptide binds to an αvβ3 and/or VLA-6 integrin.

6. The hydrogel composition of claim 1, wherein the biocompatible polymer comprises an agarose gel, polyethylene glycol, alginate, hyaluronic acid, polyacrylic acid, polyacrylic amide, polyvinyl alcohol, polyhydroxyethyl methacrylate, methacrylated dextrans, poly(N-isopropylacrylamide), or any combination thereof.

7. The hydrogel composition of claim 1, wherein the biocompatible polymer is oxidized alginate.

8. The hydrogel composition of claim 1, wherein the hydrogel composition is an injectable composition.

9. A method of promoting angiogenesis in a subject in need thereof, comprising administering to the subject the hydrogel composition of claim 1, in an amount effective to promote angiogenesis.

10. A method of promoting endothelial cell adhesion, endothelial cell spreading, endothelial cell migration and/or endothelial cell proliferation, comprising administering to the subject the hydrogel composition of claim 1, in an amount effective to promote endothelial cell adhesion, endothelial cell spreading, endothelial cell migration and/or endothelial cell proliferation.

11. A method of treating ischemic injury in a subject in need thereof, comprising administering to the subject the hydrogel composition of claim 1, in an amount effective to treat ischemic injury.

12. A method of promoting tissue regeneration in a subject in need thereof, comprising administering to the subject the hydrogel composition of claim 1, in an amount effective to promote tissue regeneration.

13. A method of bioprinting, comprising administering the hydrogel composition of claim 1 to a substrate in an amount effective to promote tissue regeneration.

14. A biomaterial product for bioprinting, comprising the hydrogel composition of claim 1.

* * * * *

UNITED STATES PATENT AND TRADEMARK OFFICE
CERTIFICATE OF CORRECTION

PATENT NO. : 11,150,251 B2
APPLICATION NO. : 15/726766
DATED : October 19, 2021
INVENTOR(S) : Mei et al.

Page 1 of 1

It is certified that error appears in the above-identified patent and that said Letters Patent is hereby corrected as shown below:

In the Specification

Column 5, Line 10: Please correct "urn" to read -- um --

Column 19, Line 15: Please correct "DG" to read -- (RDG) --

Column 21, Line 9: Please correct "laminin 14" to read -- laminin β4 --

Column 21, Line 35: Please correct "laminin 14" to read -- laminin β4 --

Column 24, Lines 17-19: Please correct "*Additionally, parasitic infections that can be treated using the sanitizing compositions of the present invention can be caused by parasites including, but not limited to,*" to read -- Additionally, parasitic infections that can be treated using the sanitizing compositions of the present invention can be caused by parasites including, but not limited to, --

Column 24, Line 23: Please correct "*ovale,* 20 *Plasmodium*" to read -- *ovale, Plasmodium* --

Column 26, Line 39: Please correct "250 id" to read -- 250 μl --

Column 30, Line 66, Table 1: Please correct "VPLS""LYSG" to read -- VPLS↓LYSG --

Column 31, Line 57: Please correct "in vive" to read -- in vivo --

In the Claims

Column 51, Line 29, Claim 1: Please correct "SEQ ID NO6" to read -- SEQ ID NO:6 --

Signed and Sealed this
Fifteenth Day of August, 2023

Katherine Kelly Vidal
*Director of the United States Patent and Trademark Office*

SEQUENCE LISTING

```
<160> NUMBER OF SEQ ID NOS: 54

<210> SEQ ID NO 1
<211> LENGTH: 9
<212> TYPE: PRT
<213> ORGANISM: Artificial
<220> FEATURE:
<223> OTHER INFORMATION: peptide

<400> SEQUENCE: 1

Thr Phe Ala Leu Arg Gly Asp Asn Pro
1               5

<210> SEQ ID NO 2
<211> LENGTH: 9
<212> TYPE: PRT
<213> ORGANISM: Artificial
<220> FEATURE:
<223> OTHER INFORMATION: peptide

<400> SEQUENCE: 2

Thr Phe Ala Leu Arg Ala Asp Asn Pro
1               5

<210> SEQ ID NO 3
<211> LENGTH: 14
<212> TYPE: PRT
<213> ORGANISM: Artificial
<220> FEATURE:
<223> OTHER INFORMATION: peptide

<400> SEQUENCE: 3

Asp Val Glu Lys Arg Gly Asp Arg Glu Glu Ala His Val Pro
1               5                   10

<210> SEQ ID NO 4
<211> LENGTH: 11
<212> TYPE: PRT
<213> ORGANISM: Artificial
<220> FEATURE:
<223> OTHER INFORMATION: peptide

<400> SEQUENCE: 4

Ile Gln Arg Gly Asp Ile Asp Ala Met Ile Ser
1               5                   10

<210> SEQ ID NO 5
<211> LENGTH: 14
<212> TYPE: PRT
<213> ORGANISM: Artificial
<220> FEATURE:
<223> OTHER INFORMATION: peptide

<400> SEQUENCE: 5

Asp Ala Val Lys Gln Leu Gln Ala Ala Glu Arg Gly Asp Ala
1               5                   10

<210> SEQ ID NO 6
<211> LENGTH: 12
<212> TYPE: PRT
<213> ORGANISM: Artificial
<220> FEATURE:
<223> OTHER INFORMATION: peptide

<400> SEQUENCE: 6

Pro Met Gln Lys Met Arg Gly Asp Val Phe Ser Pro
1               5                   10
```

```
<210> SEQ ID NO 7
<211> LENGTH: 6
<212> TYPE: PRT
<213> ORGANISM: Artificial
<220> FEATURE:
<223> OTHER INFORMATION: peptide

<400> SEQUENCE: 7

Arg Ser Asp Gly Thr Gly
1               5

<210> SEQ ID NO 8
<211> LENGTH: 10
<212> TYPE: PRT
<213> ORGANISM: Artificial
<220> FEATURE:
<223> OTHER INFORMATION: peptide

<400> SEQUENCE: 8

Glu Ala Pro Arg Gly Asp Val Tyr Gln Gly
1               5                   10

<210> SEQ ID NO 9
<211> LENGTH: 9
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: Xaa is pyrrolysine
<220> FEATURE:
<221> NAME/KEY: MISC_FEATURE
<222> LOCATION: (9)..(9)
<223> OTHER INFORMATION: Xaa is pyrrolysine

<400> SEQUENCE: 9

Gly Leu Xaa Gly Glu Arg Gly Arg Xaa
1               5

<210> SEQ ID NO 10
<211> LENGTH: 9
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: Xaa is pyrrolysine

<400> SEQUENCE: 10

Gly Phe Xaa Gly Glu Arg Gly Val Gln
1               5

<210> SEQ ID NO 11
<211> LENGTH: 4
<212> TYPE: PRT
<213> ORGANISM: Artificial
<220> FEATURE:
<223> OTHER INFORMATION: peptide

<400> SEQUENCE: 11

Asp Gly Glu Ala
1
```

<210> SEQ ID NO 12
<211> LENGTH: 6
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (3)..(3)
<223> OTHER INFORMATION: Xaa is pyrrolysine

<400> SEQUENCE: 12

Gly Phe Xaa Gly Glu Arg
1               5

<210> SEQ ID NO 13
<211> LENGTH: 6
<212> TYPE: PRT
<213> ORGANISM: Artificial
<220> FEATURE:
<223> OTHER INFORMATION: peptide

<400> SEQUENCE: 13

Gly Leu Lys Gly Glu Asn
1               5

<210> SEQ ID NO 14
<211> LENGTH: 3
<212> TYPE: PRT
<213> ORGANISM: Artificial
<220> FEATURE:
<223> OTHER INFORMATION: peptide

<400> SEQUENCE: 14

Leu Asp Val
1

<210> SEQ ID NO 15
<211> LENGTH: 4
<212> TYPE: PRT
<213> ORGANISM: Artificial
<220> FEATURE:
<223> OTHER INFORMATION: peptide

<400> SEQUENCE: 15

Arg Glu Asp Val
1

<210> SEQ ID NO 16
<211> LENGTH: 7
<212> TYPE: PRT
<213> ORGANISM: Artificial
<220> FEATURE:
<223> OTHER INFORMATION: peptide

<400> SEQUENCE: 16

Pro Glu Asp Gly Ile His Glu
1               5

<210> SEQ ID NO 17
<211> LENGTH: 5
<212> TYPE: PRT
<213> ORGANISM: Artificial
<220> FEATURE:
<223> OTHER INFORMATION: peptide

<400> SEQUENCE: 17

Pro His Ser Arg Asn

```
1               5

<210> SEQ ID NO 18
<211> LENGTH: 5
<212> TYPE: PRT
<213> ORGANISM: Artificial
<220> FEATURE:
<223> OTHER INFORMATION: peptide

<400> SEQUENCE: 18

Ala Leu Asn Gly Arg
1               5

<210> SEQ ID NO 19
<211> LENGTH: 6
<212> TYPE: PRT
<213> ORGANISM: Artificial
<220> FEATURE:
<223> OTHER INFORMATION: peptide

<400> SEQUENCE: 19

Ile Ala Phe Gln Arg Asn
1               5

<210> SEQ ID NO 20
<211> LENGTH: 5
<212> TYPE: PRT
<213> ORGANISM: Artificial
<220> FEATURE:
<223> OTHER INFORMATION: peptide

<400> SEQUENCE: 20

Ile Lys Leu Leu Ile
1               5

<210> SEQ ID NO 21
<211> LENGTH: 6
<212> TYPE: PRT
<213> ORGANISM: Artificial
<220> FEATURE:
<223> OTHER INFORMATION: peptide

<400> SEQUENCE: 21

Ser Ile Lys Val Ala Val
1               5

<210> SEQ ID NO 22
<211> LENGTH: 12
<212> TYPE: PRT
<213> ORGANISM: Artificial
<220> FEATURE:
<223> OTHER INFORMATION: peptide

<400> SEQUENCE: 22

Ala Gly Gln Trp His Arg Val Ser Val Arg Trp Gly
1               5                   10

<210> SEQ ID NO 23
<211> LENGTH: 12
<212> TYPE: PRT
<213> ORGANISM: Artificial
<220> FEATURE:
<223> OTHER INFORMATION: peptide

<400> SEQUENCE: 23

Thr Trp Ser Gln Lys Ala Leu His His Arg Val Pro
1               5                   10
```

```
<210> SEQ ID NO 24
<211> LENGTH: 7
<212> TYPE: PRT
<213> ORGANISM: Artificial
<220> FEATURE:
<223> OTHER INFORMATION: peptide

<400> SEQUENCE: 24

Ser Ile Tyr Ile Thr Arg Phe
1               5

<210> SEQ ID NO 25
<211> LENGTH: 12
<212> TYPE: PRT
<213> ORGANISM: Artificial
<220> FEATURE:
<223> OTHER INFORMATION: peptide

<400> SEQUENCE: 25

Ser Tyr Trp Tyr Arg Ile Glu Ala Ser Arg Thr Gly
1               5                   10

<210> SEQ ID NO 26
<211> LENGTH: 5
<212> TYPE: PRT
<213> ORGANISM: Artificial
<220> FEATURE:
<223> OTHER INFORMATION: peptide

<400> SEQUENCE: 26

Tyr Ile Gly Ser Arg
1               5

<210> SEQ ID NO 27
<211> LENGTH: 10
<212> TYPE: PRT
<213> ORGANISM: Artificial
<220> FEATURE:
<223> OTHER INFORMATION: peptide

<400> SEQUENCE: 27

Arg Asp Ile Ala Glu Ile Ile Lys Asp Ile
1               5                   10

<210> SEQ ID NO 28
<211> LENGTH: 8
<212> TYPE: PRT
<213> ORGANISM: Artificial
<220> FEATURE:
<223> OTHER INFORMATION: peptide

<400> SEQUENCE: 28

Val Phe Asp Asn Phe Val Leu Lys
1               5

<210> SEQ ID NO 29
<211> LENGTH: 8
<212> TYPE: PRT
<213> ORGANISM: Artificial
<220> FEATURE:
<223> OTHER INFORMATION: peptide

<400> SEQUENCE: 29

Ala Glu Ile Asp Gly Ile Glu Leu
1               5
```

<210> SEQ ID NO 30
<211> LENGTH: 11
<212> TYPE: PRT
<213> ORGANISM: Artificial
<220> FEATURE:
<223> OTHER INFORMATION: peptide

<400> SEQUENCE: 30

Ser Glu Thr Gln Arg Gly Asp Val Phe Val Pro
1               5                   10

<210> SEQ ID NO 31
<211> LENGTH: 9
<212> TYPE: PRT
<213> ORGANISM: Artificial
<220> FEATURE:
<223> OTHER INFORMATION: peptide

<400> SEQUENCE: 31

Pro Ala Ser Tyr Arg Gly Asp Ser Cys
1               5

<210> SEQ ID NO 32
<211> LENGTH: 10
<212> TYPE: PRT
<213> ORGANISM: Artificial
<220> FEATURE:
<223> OTHER INFORMATION: peptide

<400> SEQUENCE: 32

Val Thr Gly Arg Gly Asp Ser Pro Ala Ser
1               5                   10

<210> SEQ ID NO 33
<211> LENGTH: 5
<212> TYPE: PRT
<213> ORGANISM: Artificial
<220> FEATURE:
<223> OTHER INFORMATION: peptide

<400> SEQUENCE: 33

Arg Gly Asp Ser Pro
1               5

<210> SEQ ID NO 34
<211> LENGTH: 5
<212> TYPE: PRT
<213> ORGANISM: Artificial
<220> FEATURE:
<223> OTHER INFORMATION: peptide

<400> SEQUENCE: 34

Arg Asp Gly Ser Pro
1               5

<210> SEQ ID NO 35
<211> LENGTH: 4
<212> TYPE: PRT
<213> ORGANISM: Artificial
<220> FEATURE:
<223> OTHER INFORMATION: peptide

<400> SEQUENCE: 35

Arg Gly Asp Ser
1

```
<210> SEQ ID NO 36
<211> LENGTH: 3
<212> TYPE: PRT
<213> ORGANISM: Artificial
<220> FEATURE:
<223> OTHER INFORMATION: peptide

<400> SEQUENCE: 36

Arg Gly Asp
1

<210> SEQ ID NO 37
<211> LENGTH: 12
<212> TYPE: PRT
<213> ORGANISM: Artificial
<220> FEATURE:
<223> OTHER INFORMATION: peptide

<400> SEQUENCE: 37

Pro Gln Val Thr Arg Gly Asp Val Phe Thr Met Pro
1               5                   10

<210> SEQ ID NO 38
<211> LENGTH: 15
<212> TYPE: PRT
<213> ORGANISM: Artificial
<220> FEATURE:
<223> OTHER INFORMATION: peptide

<400> SEQUENCE: 38

Lys Leu Thr Trp Gln Glu Leu Tyr Gln Leu Lys Tyr Lys Gly Ile
1               5                   10                  15

<210> SEQ ID NO 39
<211> LENGTH: 35
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (23)..(25)
<223> OTHER INFORMATION: Xaa is aminohexanoic acid

<400> SEQUENCE: 39

Cys Val Arg Lys Ile Glu Ile Val Arg Lys Lys Cys Val Arg Lys Ile
1               5                   10                  15

Glu Ile Val Arg Lys Lys Xaa Xaa Xaa Arg Lys Arg Lys Leu Glu Arg
            20                  25                  30

Ile Ala Arg
        35

<210> SEQ ID NO 40
<211> LENGTH: 8
<212> TYPE: PRT
<213> ORGANISM: Artificial
<220> FEATURE:
<223> OTHER INFORMATION: peptide

<400> SEQUENCE: 40

Cys His His His Arg His Ser Phe
1               5

<210> SEQ ID NO 41
<211> LENGTH: 22
<212> TYPE: PRT
<213> ORGANISM: Artificial
```

<220> FEATURE:
<223> OTHER INFORMATION: peptide

<400> SEQUENCE: 41

Gly Pro Gln Gly Ile Ala Gly Lys Leu Thr Trp Gln Glu Leu Tyr Gln
1               5                   10                  15

Leu Lys Tyr Lys Gly Ile
            20

<210> SEQ ID NO 42
<211> LENGTH: 7
<212> TYPE: PRT
<213> ORGANISM: Artificial
<220> FEATURE:
<223> OTHER INFORMATION: peptide

<400> SEQUENCE: 42

Pro Glu Ser Leu Arg Ala Gly
1               5

<210> SEQ ID NO 43
<211> LENGTH: 8
<212> TYPE: PRT
<213> ORGANISM: Artificial
<220> FEATURE:
<223> OTHER INFORMATION: peptide

<400> SEQUENCE: 43

Gly Pro Gln Gly Ile Trp Gly Gln
1               5

<210> SEQ ID NO 44
<211> LENGTH: 8
<212> TYPE: PRT
<213> ORGANISM: Artificial
<220> FEATURE:
<223> OTHER INFORMATION: peptide

<400> SEQUENCE: 44

Val Pro Leu Ser Leu Tyr Ser Gly
1               5

<210> SEQ ID NO 45
<211> LENGTH: 7
<212> TYPE: PRT
<213> ORGANISM: Artificial
<220> FEATURE:
<223> OTHER INFORMATION: peptide

<400> SEQUENCE: 45

Gly Gly Arg Gly Asp Ser Pro
1               5

<210> SEQ ID NO 46
<211> LENGTH: 9
<212> TYPE: PRT
<213> ORGANISM: Artificial
<220> FEATURE:
<223> OTHER INFORMATION: peptide

<400> SEQUENCE: 46

Gly Gly Gly Gly Arg Gly Asp Ser Pro
1               5

<210> SEQ ID NO 47
<211> LENGTH: 9

```
<212> TYPE: PRT
<213> ORGANISM: Artificial
<220> FEATURE:
<223> OTHER INFORMATION: peptide

<400> SEQUENCE: 47

Gly Gly Gly Gly Arg Asp Gly Ser Pro
1               5

<210> SEQ ID NO 48
<211> LENGTH: 11
<212> TYPE: PRT
<213> ORGANISM: Artificial
<220> FEATURE:
<223> OTHER INFORMATION: peptide

<400> SEQUENCE: 48

Gly Gly Gly Gly Gly Gly Arg Gly Asp Ser Pro
1               5                   10

<210> SEQ ID NO 49
<211> LENGTH: 15
<212> TYPE: PRT
<213> ORGANISM: Artificial
<220> FEATURE:
<223> OTHER INFORMATION: peptide

<400> SEQUENCE: 49

Cys Gln Ala Gly Thr Phe Ala Leu Arg Gly Asp Asn Pro Gln Gly
1               5                   10                  15

<210> SEQ ID NO 50
<211> LENGTH: 10
<212> TYPE: PRT
<213> ORGANISM: Artificial
<220> FEATURE:
<223> OTHER INFORMATION: peptide

<400> SEQUENCE: 50

Leu Pro Ser His Tyr Arg Ala Arg Asn Ile
1               5                   10

<210> SEQ ID NO 51
<211> LENGTH: 11
<212> TYPE: PRT
<213> ORGANISM: Artificial
<220> FEATURE:
<223> OTHER INFORMATION: peptide

<400> SEQUENCE: 51

Gly Gly Gly Gly Pro Glu Ser Leu Arg Ala Gly
1               5                   10

<210> SEQ ID NO 52
<211> LENGTH: 12
<212> TYPE: PRT
<213> ORGANISM: Artificial
<220> FEATURE:
<223> OTHER INFORMATION: peptide

<400> SEQUENCE: 52

Gly Gly Gly Gly Gly Pro Gln Gly Ile Trp Gly Gln
1               5                   10

<210> SEQ ID NO 53
<211> LENGTH: 12
<212> TYPE: PRT
```

```
<213> ORGANISM: Artificial
<220> FEATURE:
<223> OTHER INFORMATION: peptide

<400> SEQUENCE: 53

Gly Gly Gly Gly Val Pro Leu Ser Leu Tyr Ser Gly
1               5                   10

<210> SEQ ID NO 54
<211> LENGTH: 8
<212> TYPE: PRT
<213> ORGANISM: Artificial
<220> FEATURE:
<223> OTHER INFORMATION: peptide

<400> SEQUENCE: 54

Gly Gly Gly Gly Gly Gly Gly Gly
1               5
```